United States Patent
Almarode et al.

(10) Patent No.: US 12,300,357 B2
(45) Date of Patent: May 13, 2025

(54) APPLIED COMPUTER TECHNOLOGY FOR MANAGEMENT, SYNTHESIS, VISUALIZATION, AND EXPLORATION OF PARAMETERS IN LARGE MULTI-PARAMETER DATA SETS

(71) Applicant: FlowJo, LLC, Ashland, OR (US)

(72) Inventors: James Edward Almarode, Lebanon, OR (US); Josef Spidlen, Coquitlam (CA); Michael David Stadnisky, Ashland, OR (US)

(73) Assignee: FlowJo, LLC, Ashland, OR (US)

( * ) Notice: Subject to any disclaimer, the term of this patent is extended or adjusted under 35 U.S.C. 154(b) by 1083 days.

(21) Appl. No.: 15/838,724

(22) Filed: Dec. 12, 2017

(65) Prior Publication Data

US 2018/0165414 A1 Jun. 14, 2018

Related U.S. Application Data

(60) Provisional application No. 62/433,930, filed on Dec. 14, 2016.

(51) Int. Cl.

| | |
|---|---|
| *G16B 45/00* | (2019.01) |
| *C12N 15/10* | (2006.01) |
| *G01N 15/10* | (2024.01) |
| *G01N 15/14* | (2024.01) |
| *G01N 33/48* | (2006.01) |
| *G16B 25/00* | (2019.01) |
| *G16B 50/00* | (2019.01) |
| *G16B 50/10* | (2019.01) |
| *G16B 50/30* | (2019.01) |

(52) U.S. Cl.
CPC ............ *G16B 45/00* (2019.02); *C12N 15/10* (2013.01); *C12N 15/1089* (2013.01); *G01N 15/10* (2013.01); *G01N 33/48* (2013.01); *G16B 25/00* (2019.02); *G16B 50/00* (2019.02); *G16B 50/10* (2019.02); *G16B 50/30* (2019.02); *G01N 2015/1006* (2013.01); *G01N 2015/1402* (2013.01)

(58) Field of Classification Search
None
See application file for complete search history.

(56) References Cited

U.S. PATENT DOCUMENTS

| | | | |
|---|---|---|---|
| 4,845,653 | A | 7/1989 | Conrad et al. |
| 5,627,040 | A | 5/1997 | Bierre et al. |
| 5,739,000 | A | 4/1998 | Bierre et al. |
| 5,795,727 | A | 8/1998 | Bierre et al. |
| 5,962,238 | A | 10/1999 | Sizto et al. |
| 6,014,904 | A | 1/2000 | Lock |
| 6,221,592 | B1 | 4/2001 | Schwartz et al. |
| 6,560,546 | B1 | 5/2003 | Shenk et al. |
| 6,769,030 | B1 | 7/2004 | Bournas |
| 6,944,338 | B2 | 9/2005 | Lock et al. |
| 7,010,582 | B1 | 3/2006 | Cheng et al. |
| 7,194,531 | B2 | 3/2007 | Donker et al. |
| 7,277,938 | B2 | 10/2007 | Duimovich et al. |
| 7,356,598 | B1 | 4/2008 | Giroir et al. |
| 7,472,342 | B2 | 12/2008 | Haut et al. |
| 7,492,372 | B2 | 2/2009 | Abshear |
| 8,835,358 | B2 | 9/2014 | Fodor et al. |
| 9,567,645 | B2 | 2/2017 | Fan et al. |
| 9,762,598 | B1 | 9/2017 | Jagpal et al. |
| 2002/0067358 | A1 | 6/2002 | Casara et al. |
| 2003/0009470 | A1 | 1/2003 | Leary |
| 2003/0078703 | A1 | 4/2003 | Potts et al. |
| 2003/0088657 | A1 | 5/2003 | Eggers |
| 2004/0019690 | A1 | 1/2004 | Cardno et al. |
| 2004/0061713 | A1 | 4/2004 | Jennings |
| 2004/0161767 | A1 | 8/2004 | Baldwin et al. |
| 2004/0242216 | A1 | 12/2004 | Boutsikakis |
| 2004/0250118 | A1 | 12/2004 | Andreev et al. |
| 2005/0038608 | A1 | 2/2005 | Chandra et al. |
| 2005/0239125 | A1 | 10/2005 | Hodge |
| 2005/0247114 | A1 | 11/2005 | Kahn et al. |
| 2005/0272085 | A1 | 12/2005 | Hodge |
| 2006/0014192 | A1 | 1/2006 | Hodge |
| 2006/0063264 | A1 | 3/2006 | Turner et al. |
| 2006/0148063 | A1 | 7/2006 | Fauzzi et al. |

(Continued)

FOREIGN PATENT DOCUMENTS

| | | |
|---|---|---|
| JP | 62-31815 | 2/1987 |
| JP | 63-259442 | 10/1988 |

(Continued)

OTHER PUBLICATIONS

Archival Cytometry Standard, Oct. 13, 2010, International Society for Advancement of Cytometry Candidate Recommendation (draft), version 1000929, downloaded from http://flowcyt.sf.net/acs/latest.pdf.

(Continued)

*Primary Examiner* — Joseph Woitach

(74) *Attorney, Agent, or Firm* — Knobbe, Martens, Olson & Bear, LLP

(57) ABSTRACT

Computer technology is disclosed that applies innovative data processing and visualization techniques to large multi-parameter data sets such as cellular gene expression data to find new relationships such as relationships between cells and genes and create new associative data structures within the data sets that represent these relationships. For example, scatterplots of gene expression data can be iteratively pivoted between a cell view and a gene view to find cell populations and gene sets of interest to a user.

25 Claims, 26 Drawing Sheets

(56) References Cited

U.S. PATENT DOCUMENTS

| | | |
|---|---|---|
| 2007/0014305 A1 | 1/2007 | Assad |
| 2007/0031823 A1 | 2/2007 | Bentwich |
| 2007/0041395 A1 | 2/2007 | Boucek |
| 2007/0128633 A1 | 6/2007 | Zozulya et al. |
| 2007/0219728 A1 | 9/2007 | Papageorgiou et al. |
| 2008/0097917 A1 | 4/2008 | Dicks et al. |
| 2008/0109175 A1 | 5/2008 | Michalak |
| 2008/0154513 A1 | 6/2008 | Kovatchev |
| 2008/0212643 A1 | 9/2008 | McGahhey et al. |
| 2008/0263468 A1 | 10/2008 | Cappione et al. |
| 2009/0070841 A1 | 3/2009 | Buga et al. |
| 2009/0192363 A1 | 7/2009 | Case |
| 2009/0204557 A1 | 8/2009 | Zhang |
| 2009/0246782 A1 | 10/2009 | Kelso et al. |
| 2009/0307757 A1 | 12/2009 | Groten |
| 2010/0042351 A1 | 2/2010 | Covey et al. |
| 2010/0043047 A1 | 2/2010 | Archer et al. |
| 2010/0070459 A1 | 3/2010 | Zigon et al. |
| 2010/0070904 A1 | 3/2010 | Zigon et al. |
| 2010/0161561 A1 | 6/2010 | Moore et al. |
| 2010/0254581 A1 | 10/2010 | Neeser et al. |
| 2011/0066385 A1 | 3/2011 | Rajwa et al. |
| 2011/0099497 A1 | 4/2011 | Fok et al. |
| 2011/0191899 A1 | 8/2011 | Ainley et al. |
| 2011/0282870 A1 | 11/2011 | Herzenberg et al. |
| 2012/0029832 A1 | 2/2012 | Dodgson |
| 2012/0140641 A1 | 6/2012 | Reese et al. |
| 2012/0179779 A1 | 7/2012 | Awasthi |
| 2012/0214190 A1 | 8/2012 | Hou |
| 2012/0215481 A1 | 8/2012 | Covey et al. |
| 2012/0239297 A1 | 9/2012 | Yokota et al. |
| 2012/0245889 A1 | 9/2012 | Zhu et al. |
| 2013/0091135 A1 | 4/2013 | Yokoi et al. |
| 2013/0117298 A1 | 5/2013 | Ray |
| 2013/0177933 A1 | 7/2013 | Malisauskas |
| 2013/0197894 A1 | 8/2013 | Sablinski |
| 2013/0226813 A1 | 8/2013 | Voltz |
| 2013/0289925 A1 | 10/2013 | Jiang et al. |
| 2014/0072189 A1 | 3/2014 | Jena et al. |
| 2014/0154789 A1 | 6/2014 | Polwart et al. |
| 2014/0164564 A1 | 6/2014 | Hoofnagle et al. |
| 2014/0213468 A1 | 7/2014 | Ehrenkranz et al. |
| 2014/0216128 A1 | 8/2014 | Trotter |
| 2014/0222866 A1 | 8/2014 | Joneja |
| 2015/0120883 A1 | 4/2015 | Gurtowski |
| 2015/0295972 A1 | 10/2015 | Hagan |
| 2015/0363563 A1 | 12/2015 | Hallwachs |
| 2016/0122341 A1 | 5/2016 | Vakalopoulos et al. |
| 2016/0130574 A1 | 5/2016 | Sadekova et al. |
| 2016/0170980 A1 | 6/2016 | Stadnisky et al. |
| 2016/0243251 A1 | 8/2016 | Blainey et al. |
| 2016/0328249 A1 | 11/2016 | Simm et al. |
| 2016/0337786 A1 | 11/2016 | Kafle et al. |
| 2016/0362408 A1 | 12/2016 | Vakalopoulos et al. |
| 2016/0370350 A1 | 12/2016 | Rajwa et al. |
| 2017/0102310 A1 | 4/2017 | Xu |
| 2018/0010134 A1 | 1/2018 | Sharp et al. |
| 2018/0340890 A1 | 11/2018 | Roederer et al. |

FOREIGN PATENT DOCUMENTS

| | | |
|---|---|---|
| JP | 05-209821 | 8/1993 |
| JP | 2001-511546 | 8/2001 |
| JP | 2005-352771 | 12/2005 |
| JP | 2006-230333 | 9/2006 |
| JP | 2012-505460 | 3/2012 |
| WO | WO 04/072866 | 8/2004 |
| WO | WO 13/143533 | 10/2013 |
| WO | WO 14/022787 | 2/2014 |

OTHER PUBLICATIONS

International Search Report and Written Opinion dated Jun. 16, 2016 in International application No. PCT/US15/65045.

Amir, El-ad David et al. "viSNE enables visualization of high dimensional single-cell data and reveals phenotypic heterogeneity of leukemia." *Nature biotechnology* 31.6 (2013): 545-552.

Bauer et al. (eds.), Clinical Flow Cytometry: Principles and Applications, Williams & Wilkins (1993).

Hsiao et al. "Mapping cell populations in flow cytometry data for cross-sample comparision using the Friedman-Rafsky test statistic as a distance meaure: FCM Cross-Sample Comparision." Cytometry, Part A, vol. 89, No. 1, pp. 71-88, Aug. 14, 2015.

International Search Report for International Application No. PCT/US2017/065987 dated Feb. 23, 2018.

International Search Report for International Application No. PCT/US2018/034199 dated Jul. 26, 2018.

Jaroszeski et al. (eds.), Flow Cytometry Protocols, Methods in Molecular Biology No. 91, Humana Press (1998).

Landy et al. (eds.), Clinical Flow Cytometry, Annals of the New York Academy of Sciences vol. 677 (1993).

Macosko, Evan Z et al. "Highly parallel genome-wide expression profiling of individual cells using nanoliter droplets." *Cell* 161.5 (2015): 1202-1214.

Newell et. al. Cytometry by Time-of-Flight Shows Combinatorial Cytokine Expression and Virus-Specific Cell Niches within a Continuum of CD8+ T Cell Phenotypes Immunity, 2012.

Ormerod (ed.), Flow Cytometry: A Practical Approach, Oxford Univ. Press (1994).

Pawley (ed.), Handbook of Biological Confocal Microscopy, 2nd Edition, Plenum Press (1989).

R. E. Bellman; Rand Corporation (1957). Dynamic Programming. Princeton University Press. Republished: Richard Ernest Bellman (2003). Dynamic Programming. Courier Dover Publications. & Richard Ernest Bellman (1961). Adaptive Control Processes: a guided tour. Princeton University Press.].

Roederer et. al. The genetic architecture of the human immune system: a bioresource for autoimmunity and disease pathogenesis. Cell. Apr. 9, 2015;161(2):387-403. doi: 10.1016/j.cell.2015.02.046. Epub Mar. 12, 2015.

Roederer et al. "Frequency difference gating: A multivariate method for identifying subsets that differ between samples." Cytometry. vol. 45, No. 1, pp. 56-64, Aug. 24, 2001.

Roderer et al. "Probability binning comparison: a metric for quantitating multivariate distribution differences." Cytometry, vol. 45, No. 1, pp. 47-55, Aug. 24, 2001.

Shapiro, Howard. Practical Flow Cytometry, 4th ed., Wiley-Liss (2003).

Shekhar, Karthik et al. "Automatic classification of cellular expression by nonlinear stochastic embedding (ACCENSE)." *Proceedings of the National Academy of Sciences* 111.1 (2014): 202-207.

Supplementary European Search Report for Application No. EP 15 86 6701 dated Jun. 21, 2018.

Tirosh, Itay et al. "Dissecting the multicellular ecosystem of metastatic melanoma by single-cell RNA-seq." *Science* 352.6282 (2016): 189-196.

Van den Bulcke, T. et al. SynTREN: A Generator of Synthetic Gene Expression Data for Design and Analysis of Structure Learning Algorithms, BMC Bioinformatics, Jan. 26, 2006; vol. 7, No. 43; pp. 1-12.

Van der Maaten, Laurens, and Geoffrey Hinton. "Visualizing data using t-SNE." *Journal of Machine Learning Research* 9.2579-2605 (2008): 85.

Van Der Maaten, Laurens, Eric Postma, and Jaap Van den Herik. "Dimensionality reduction: a comparative." *J Mach Learn Res* 10 (2009): 66-71.

DeTomaso et al., Aug. 23, 2016, FastProject: a tool for low-dimensional analysis of single-cell RNA-Seq data, BMC Bioinformatics, 17(1):1-12.

Kiselev et al., Aug. 20, 2016, 9. Seurat: analysis of single cell RNA-seq data, https://scrnaseq-course.cog.sanger.ac.uk/website/seurat-chapter.html, retrieved on Jun. 26, 2020, 37 pp.

Melamed et al., May 2, 2007, GenePattern: Multiplot (v2), https://www.genepattern.org/modules/docs/Multiplot/2, retrieved on Jun. 25, 2020, 11 pp.

Roederer, 2001, Probability binning comparison: a metric for quantitating univariate distribution differences, Cytometry, 45:37-46.

{Cell ID 1, Parameter 1 (ID, Value), Parameter 2 (ID, Value), ..., Parameter n (ID, Value)}
{Cell ID 2, Parameter 1 (ID, Value), Parameter 2 (ID, Value), ..., Parameter n (ID, Value)}
.....

| Cell | Gene 1 | Gene 2 | Gene 3 | ..... |
|------|--------|--------|--------|-------|
| ID1  | 0      | 6      | 0      | ...   |
| ID2  | 1      | 4      | 0      | ...   |
| ID3  | 3      | 5      | 2      | ...   |

.........

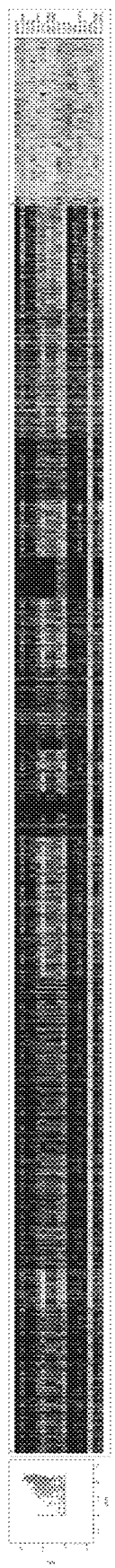
Figure 20B
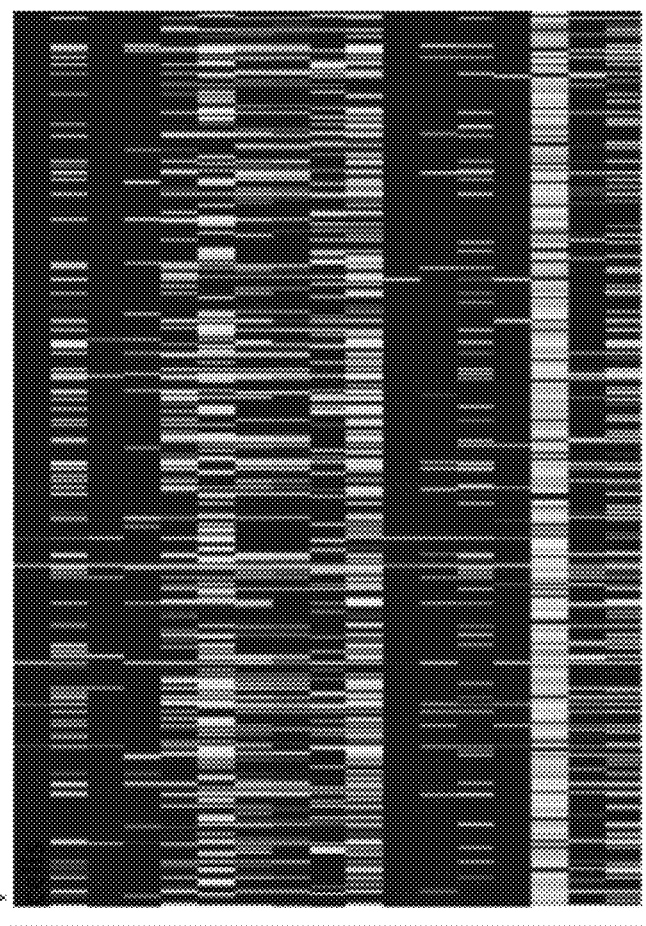
Figure 20C
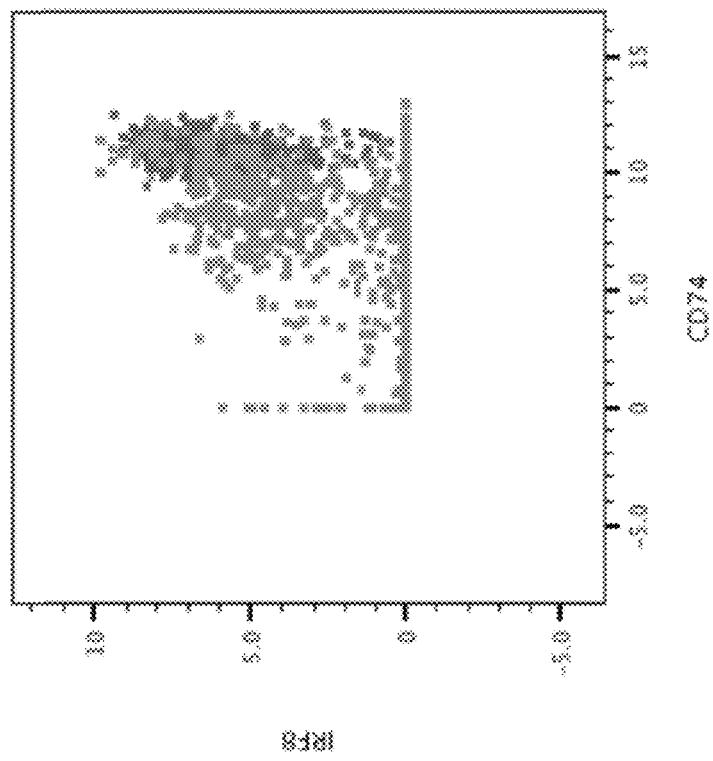

APPLIED COMPUTER TECHNOLOGY FOR MANAGEMENT, SYNTHESIS, VISUALIZATION, AND EXPLORATION OF PARAMETERS IN LARGE MULTI-PARAMETER DATA SETS

CROSS-REFERENCE AND PRIORITY CLAIM TO RELATED PATENT APPLICATION

This patent application claims priority to U.S. provisional patent application Ser. No. 62/433,930, filed Dec. 14, 2016, and entitled "Applied Computer Technology for Management, Synthesis, Visualization, and Exploration of Parameters in Large Multi-Parameter Data Sets", the entire disclosure of which is incorporated herein by reference.

INTRODUCTION

The volume of genetic and gene expression information that is available for both bulk populations and individual cells has grown to the point where it has become unwieldy for investigators. For example, cellular gene expression data can include gene expression data for thousands of genes (e.g., 10,000-30,000 or more genes), can now be measured for individual cells, and thousand cells can be measured per sample. This has presented a tremendous technical problem in the art of visualizing, analyzing, exploring, and making sense of cellular gene expression data.

For example, with conventional approaches to using computers to facilitate visualization of cellular gene expression data, the visualization is a final end point and the visualization is reached as a result of a user manually writing scripts using the R programming language, which requires the user to have knowledge of different libraries in order to perform data input, reformatting, manipulations, calculations and graphing. These scripts usually have to be customized for particular data sets, and their creation requires expert knowledge of the programming language, existing libraries, and required inputs to produce results. Moreover, such conventional approaches prevent the deep exploration of heterogeneous cell populations.

As a solution to this technical problem, the inventors disclose the application of computer technology using innovative scatterplot displays across various dimensions of cellular expression data including cell (or cell population) view scatterplots in which cells are visualized as individual data points (e.g., gene vs gene scatterplots of cells) and gene view scatterplots in which genes are visualized as individual data points (e.g., cell population vs cell population scatterplots of genes). Gating can be performed within these scatterplots to create cell populations and gene sets respectively that can serve as biologically-relevant dimensions to be added as new data objects in a workspace for use in augmenting the cellular gene expression data and opening new avenues for meaningful investigation. By way of contrast, performing such analysis in an isolated, siloed manner on the basis of individual genes quickly becomes unwieldy, whereas the ability to pivot between cell view scatterplots and gene view scatterplots allows users to find biologically-relevant grouping of genes that can then be further investigated as synthetic parameters of a cell view scatterplot.

As noted above, with conventional visualization systems in the art, the visualization serves as an endpoint in the process and cannot serve as a starting point for further creating further visualization refinements for further investigations. As an example, samples of immune cells from metastatic melanoma patients may contain T cells, and conventional visualization systems in the art would be able only to identify this subset within the immune cells. However, the innovative computer systems described herein allow for deep exploration and analysis of the T cell subset to identify multiple subsets within T cells, for example, T cells which are "exhausted", track this state to individual genes which can then be targeted to reverse this exhaustion, activate T cells, and thus possibly stimulate an immune response to eradicate the metastases, as explained in greater detail below with reference to example embodiments.

Accordingly, through the innovative visualization techniques described herein, computer technology can be applied to cellular gene expression data to find new relationships between cells and genes and create new associative data structures within the cellular gene expression data that represents these relationships.

Through these and other features, example embodiments of the invention provide significant technical advances in the applied bioinformatics arts.

BRIEF DESCRIPTION OF THE DRAWINGS

FIGS. 20A-D show example reports can be created through the system.

DETAILED DESCRIPTION OF EXAMPLE EMBODIMENTS

Figure 1:
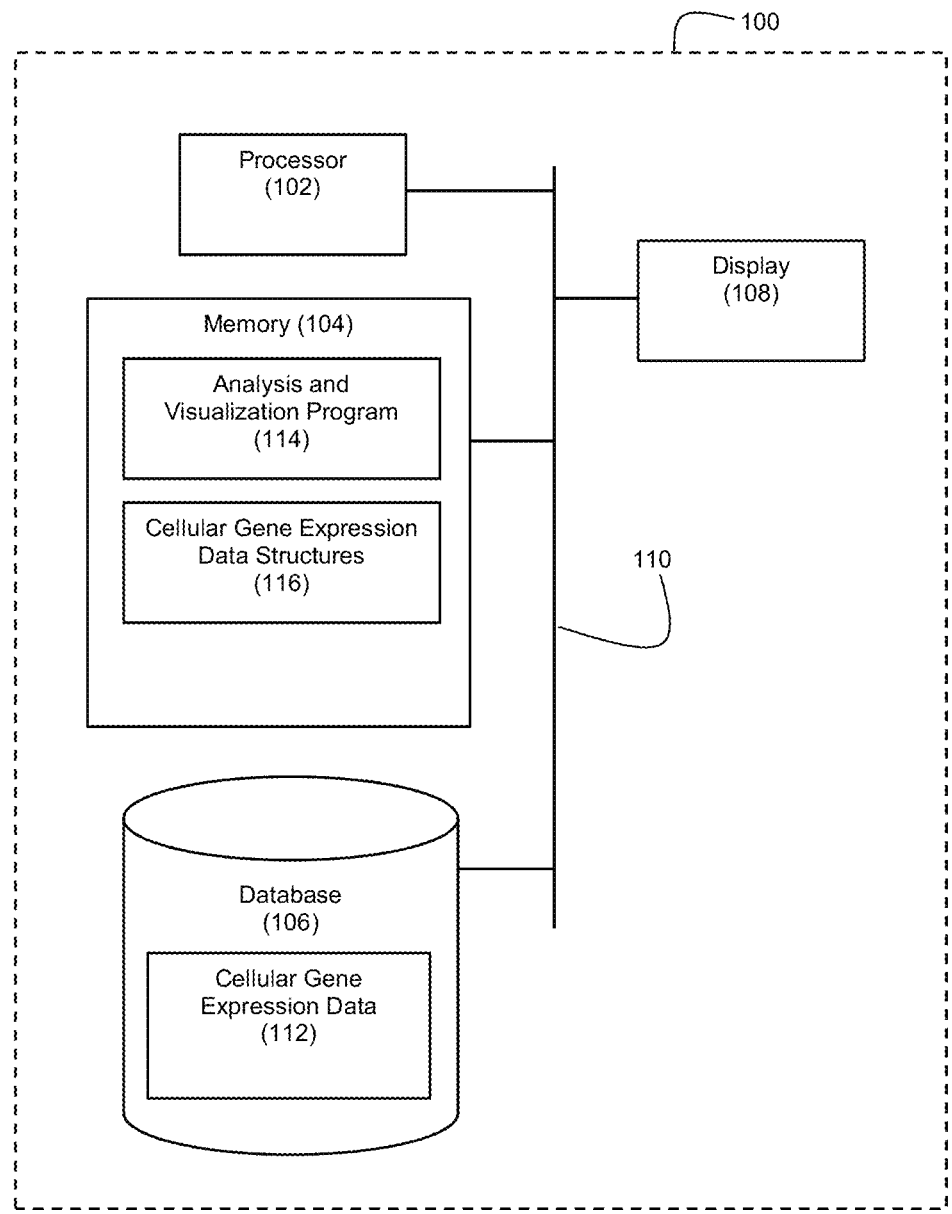
FIG. 1 discloses an example computer system that can be used to support the innovative data processing and visualization techniques described herein.

FIG. 1 discloses an example computer system 100 that can be used to support the innovative data processing and visualization techniques described herein. The example computer system 100 comprises a processor 102, memory 104, database 106, and display 108 that can be in communication with each other over an interconnect technology such as bus 110.

Processor 102 can take the form of any processor suitable for performing the operations described herein. For example, the CPU of a laptop or workstation would be suitable for use as processor 102. It should be understood that processor 102 may comprise multiple processors, including distributed processors that communicate with each other over a network to carry out tasks described herein (e.g., cloud computing processing resources). Memory 104 can take the form of any computer memory suitable for cooperating with processor 102 in the execution of the tasks described herein. It should be understood that memory 104 may take the form of multiple memory devices, including memory that is distributed across a network. Similarly, database 106 can take the form of any data repository accessible to the processor 102 (e.g., a file system on a computer, relational database, etc.), and it should be understood that database 106 may take the form of multiple distributed databases (e.g., cloud storage). Display 108 can take the form of a computer monitor or screen that is capable of generating the visualizations described herein.

The innovative data analysis and visualization techniques described herein can be performed on cellular gene expression data 112. Cellular gene expression data 112 can be generated by next-generation sequencing (e.g. for the measurement of RNA-Sequencing (RNASeq) and single cell RNA sequencing (scRNA-Seq) among other sequencing approaches). However, this is only an example, and other techniques for generating cellular gene expression data 112 may be employed. Additional examples include polymerase chain reaction approaches including digital droplet and reverse transcriptase. Still more examples include RNA measurement by flow cytometry, and microarrays, among others, that produce data files which contain the quantification of DNA and/or RNA, or through software programs that process the raw read data (primary and secondary analysis) to generate the gene expression data files. Yet another example is gene expression data derived from stochastic labeling of a sample. Examples of stochastically labeled gene expression data can be found in U.S. Pat. Nos. 9,567,645 and 8,835,358 and in patent application Ser. No. 15/715,028, filed Sep. 25, 2017, and entitled "Measurement of Protein Expression Using Reagents with Barcoded Oligonucleotide Sequences", the entire disclosures of each of which are incorporated by reference.

Furthermore, the innovative data analysis and visualization techniques described herein can be applied to data generated from single cells by a variety of means. Single cell analysis may include the stochastic labeling of nucleic acids or proteins or any combination of proteins and nucleic acids. As an example, the innovative data analysis and visualization techniques described herein may be used to analyze quantitative features of protein density or gene expression or any combination thereof. The innovative data analysis and visualization techniques described herein can also provide for an improved visualization of quantitative data generated by stochastic labeling of a variety of proteins or nucleic acids in single cells. Quantitative values of biological populations (nucleic acids, proteins etc.) in individual cells may be compared with other individual cells, or between cell types or even between methods of generating the data. For example gene expression values may be visualized as a function of the method used of generating the data set. The innovative data analysis and visualization techniques described herein can also be used to compare quantitative data generated by a variety of means described here in ways that provide for the visualization of quantitative biological population data independent of the method of generating such data.

This data 112 can be characterized as a large multi-parameter data set which poses special technical challenges in terms of difficulty in creating meaningful visualizations, particularly when considered with respect to underlying biology so that biologically-relevant information is meaningfully presented to users in a visual manner. For example, the cellular gene expression data may comprise data for large numbers of individual cells and cell populations, with parameters for each cell or cell population that may stretch into 10,000-30,000 or more parameters. Cellular gene expression data 112 can be read out of files in database 106 and loaded into memory 104 as a plurality of data structures 116 to be manipulated by processor 102 during execution of an analysis and visualization program 114. Program 114 may comprise processor-executable computer code in the form of a plurality of processor-executable instructions that are resident on a non-transitory computer-readable storage medium such as memory 104.

Figures 2A, 2B:
FIG. 2A depicts examples of cellular gene expression data sets.
FIG. 2B depicts a table view of example cellular gene expression data.

FIG. 2A depicts examples of cellular gene expression data sets where each cell (or cell population) is identified by a Cell ID and is associated with a plurality of parameters, each parameter having an ID and a value in relation to a Cell ID. As indicated, gene expression data for cells is highly dimensional and the number of parameters for each cell may reach 10,000-30,000 or more parameters, either per cell or per population of cells. Examples of parameters in the cellular data include counts of gene expression in the subject cell for a large number of genes. Thus, Parameter 1 for Cell 1 may correspond to Gene 1 and its value can be a count of expressions for Gene 1 in Cell 1. Similarly, Parameter 2 for Cell 1 may correspond to Gene 2 and its value can be a count of expressions for Gene 2 in Cell 1. FIG. 2B depicts a table view of example cellular gene expression data 112. Each row in the table 200 corresponds to a different cell (see the Cell column), and the various columns labeled Gene 1, Gene 2, etc. correspond to different genes and the table cells identify counts of gene expressions for the correspond genes in each subject cell. This table may also include parameters other than genes. For example, the cellular gene expression data 112 may include data values for parameters such as t-distributed stochastic neighbor embedding (tSNE), principal component analysis (PCA), linear discriminant analysis (LDA), etc. in each table cell, where these data values represent an analysis calculation whose value captures differences for individual cells across n parameters. The cellular gene expression data 112 can be stored in any of a number of formats (e.g., as CSV files, database tables (e.g., as relational data in a relational database), spare data representations, binary formats, and others).

Figure 3:
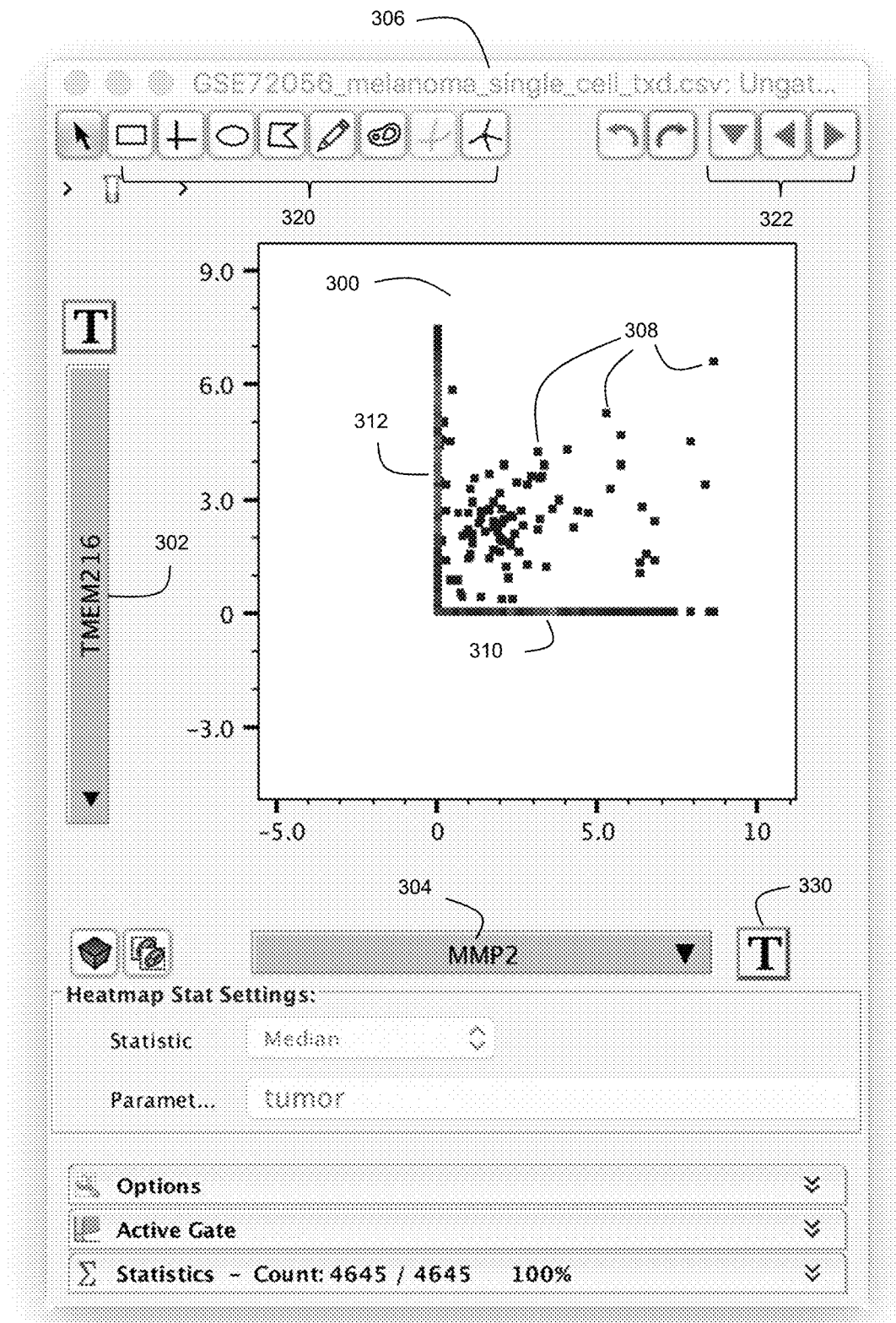
FIG. 3 depicts an example cell view graph window scatterplot.

FIG. 3 depicts an example graph window (GW) that can be produced through execution of program 114 for presentation to a user via display 108, where the graph window visualizes Gene 1 vs. Gene 2 with respect to a cell population. This visualization can be referred to as a cell view of the cellular gene expression data 112. As explained below, gating on a selection of individual cells in the cell view creates a cell population. This graph window presents a scatterplot 300 of gene expressions for two user-selected genes 302 and 304 (TMEM216 and MMP2, respectively in this example) with respect to a cell population in a user-selected file 306. Each file may correspond to a single sample of cell populations, a single cell population (e.g. one population that has been sorted by flow cytometric active cell sorting and analyzed), or possibly multiple samples which have been concatenated (from different patients, or from a patient at different points in time). Each dot 308 in the scatterplot represents a cell in the cell population of the subject file 306. The scale of the X-axis and Y-axis in this example identify counts for the corresponding gene. Thus, the position of a dot 308 on the horizontal X-axis identifies a count of how many of the gene MMP2 are present in the cell corresponding to the subject dot 308, and the position of the dot 308 on the vertical Y-axis identifies a count of how many of the gene TMEM216 are present in the cell corresponding to the subject dot 308. Thus, dots 308 in the upper right quadrant of the scatterplot 300 correspond to cells where both TMEM216 and MMP2 are highly expressed, while dots in the lower left quadrant of the scatterplot 300 correspond to cells where both TMEM216 and MMP2 are expressed at a low level. Likewise, the upper left quadrant corresponds to cells where TMEM216 is highly expressed but MMP2 is not, while the lower right quadrant corresponds to cells where MMP2 is highly expressed, but TMEM216 is not. The diagonal where y=x is where cells 308 are positioned if those cells equally express both selected genes. Thus, the distance of a cell 308 away from this diagonal in either direction indicates the extent of differential expression of the selected genes in a given cell. It is expected that for many cell populations, there will be large numbers of cells where the expression of the selected genes for those cells is at the zero level. This leads to a large clustering of dots 308 at the zero levels 310 and 312 on the X-axis and Y-axis respectively. Color coding can be used at 310 and 312 to indicate the density of cells with such zero-level gene expressions.

Figure 4:
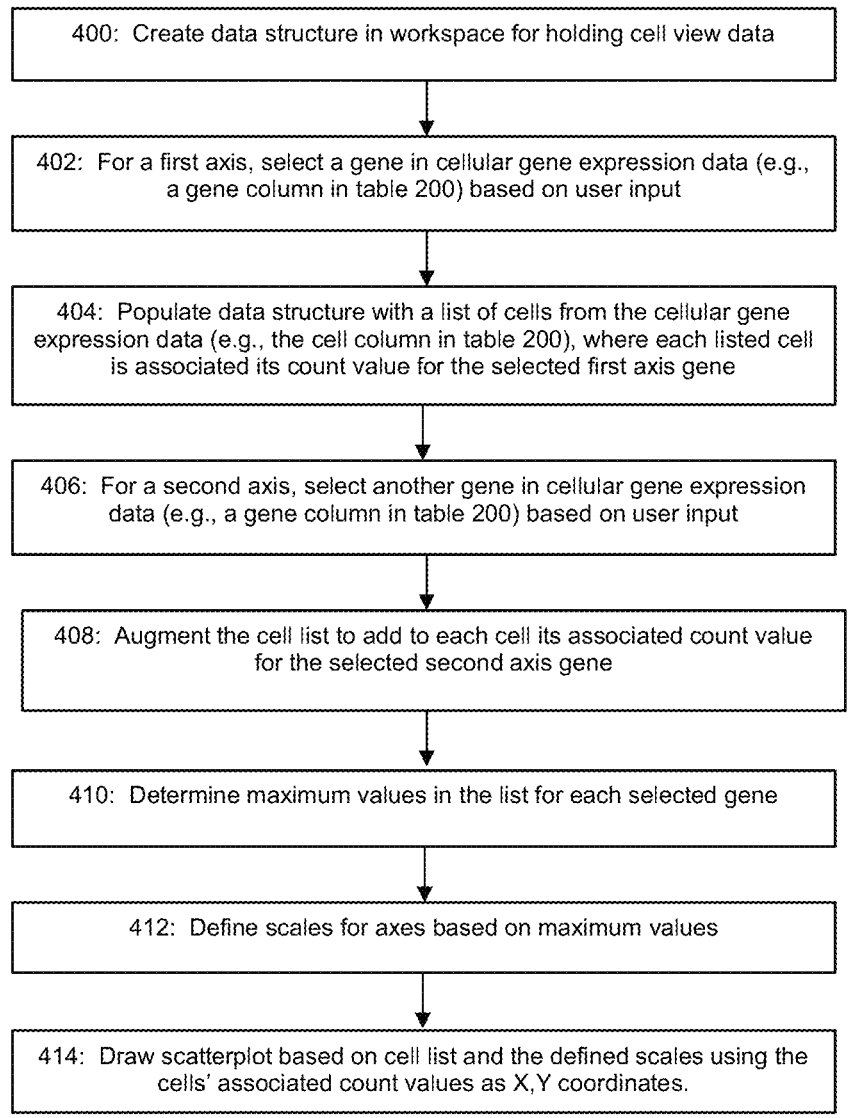
FIG. 4 depicts an example process flow for execution to create a cell view scatterplot.

FIG. 4 depicts an example process flow for execution as part of program 114 that describes how scatterplot 300 can be generated. At step 400, the processor creates a data structure in a memory workspace (see 116 in FIG. 1). This data structure can be used for holding cell view data.

Figure 5:
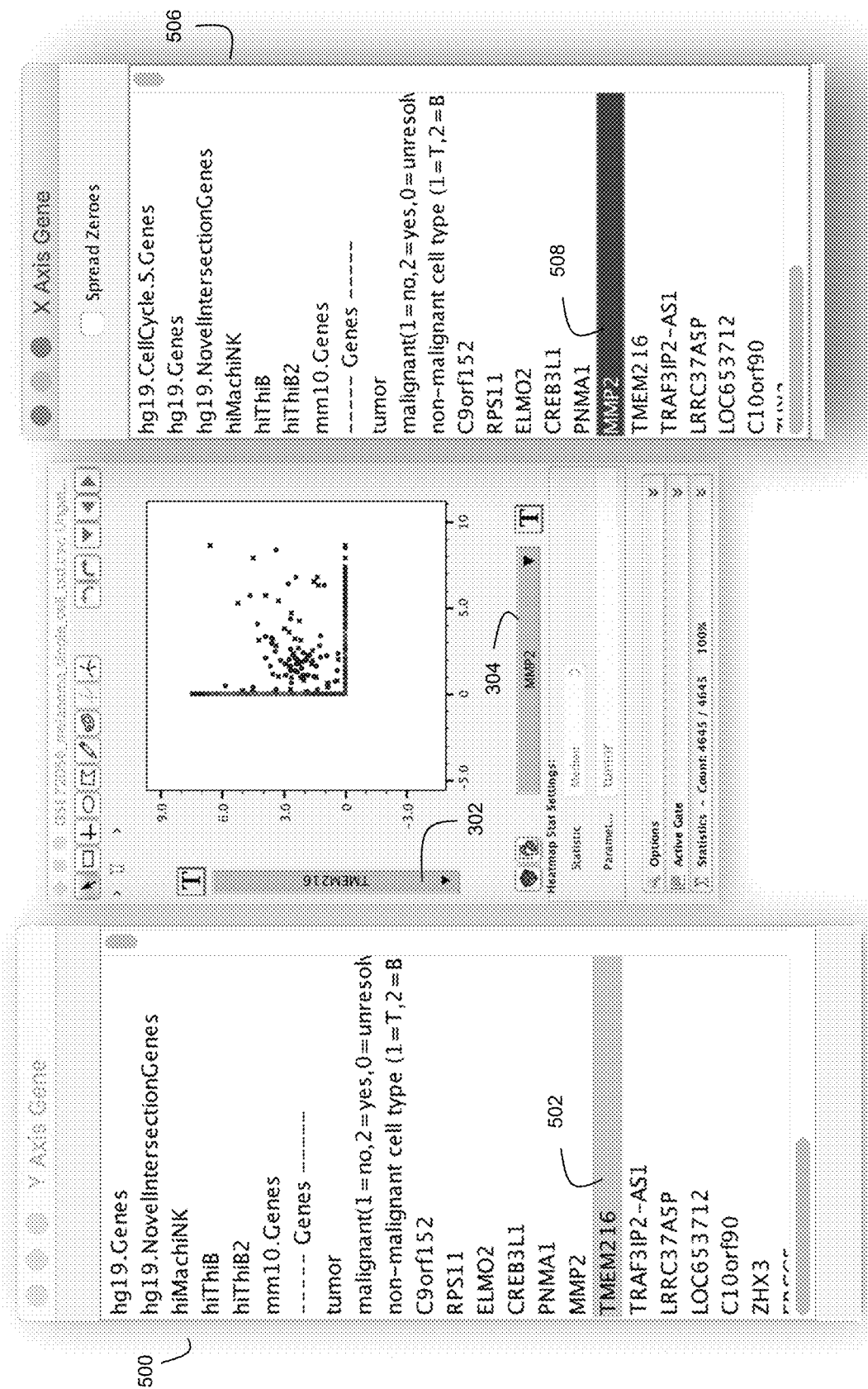
FIG. 5 shows an example cell view scatterplot user interface that includes parameter selection menus.

For a first axis, the processor selects a gene in the cellular gene expression data 112 based on user input (step 402). For example, the processor can respond to user input to select a gene column in table 200. FIG. 5 shows how the user interface can present a user with a list of genes for each axis. To access a selection menu, a user can select a gene selector 302 or 304 for the Y and X axes respectively. If we assume the first axis in this example is the Y-axis, upon selection of 302, a parameter selection menu 500 is shown which presents a list of parameters available for selection with respect to the Y-axis. This list can be populated with parameters from the cellular gene expression data 112. As shown in FIG. 5, the user selection 502 for the Y-axis gene is TMEM216. At step 404, the processor populates the data structure with a list of cells from the cellular gene expression data 112 (e.g., the cells in the cell column of table 200). Each listed cell is associated with its count value for the selected first axis gene.

For a second axis, the processor selects another gene in the cellular gene expression data 112 based on user input (step 406). For example, the processor can respond to user input to select another gene column in table 200. FIG. 5 shows an example of a user interface where 304 is selected to access an X-axis parameter selection menu 506 (resulting in selection 508 of MMP2). At step 408, the processor augments the cell list to add to each cell its associated count value for the selected second axis gene. Thus, at this point, the data structure comprises a list of cells associated with count pairs for the selected genes of the first and second axis; for example the list can comprise a set of vectors {Cell ID 1, Gene 1 Count, Gene 2 Count} for each cell in the cellular gene expression data 112.

At step 410, the process parses the list to find the maximum values for each selected gene (the highest counts). These maximum values are then used by the processor to define the appropriate scales for the X-axis and Y-axis in the scatterplot (step 412). For example, if the maximum value for the X-axis gene is 10, the X-axis scale can be from 0-10. At step 414, the processor draws the scatterplot based on the cell list and the defined scales using the cell's associated count values as X,Y coordinates in the scatterplot. The result is a scatterplot 300 as shown by FIG. 3.

Figure 6:
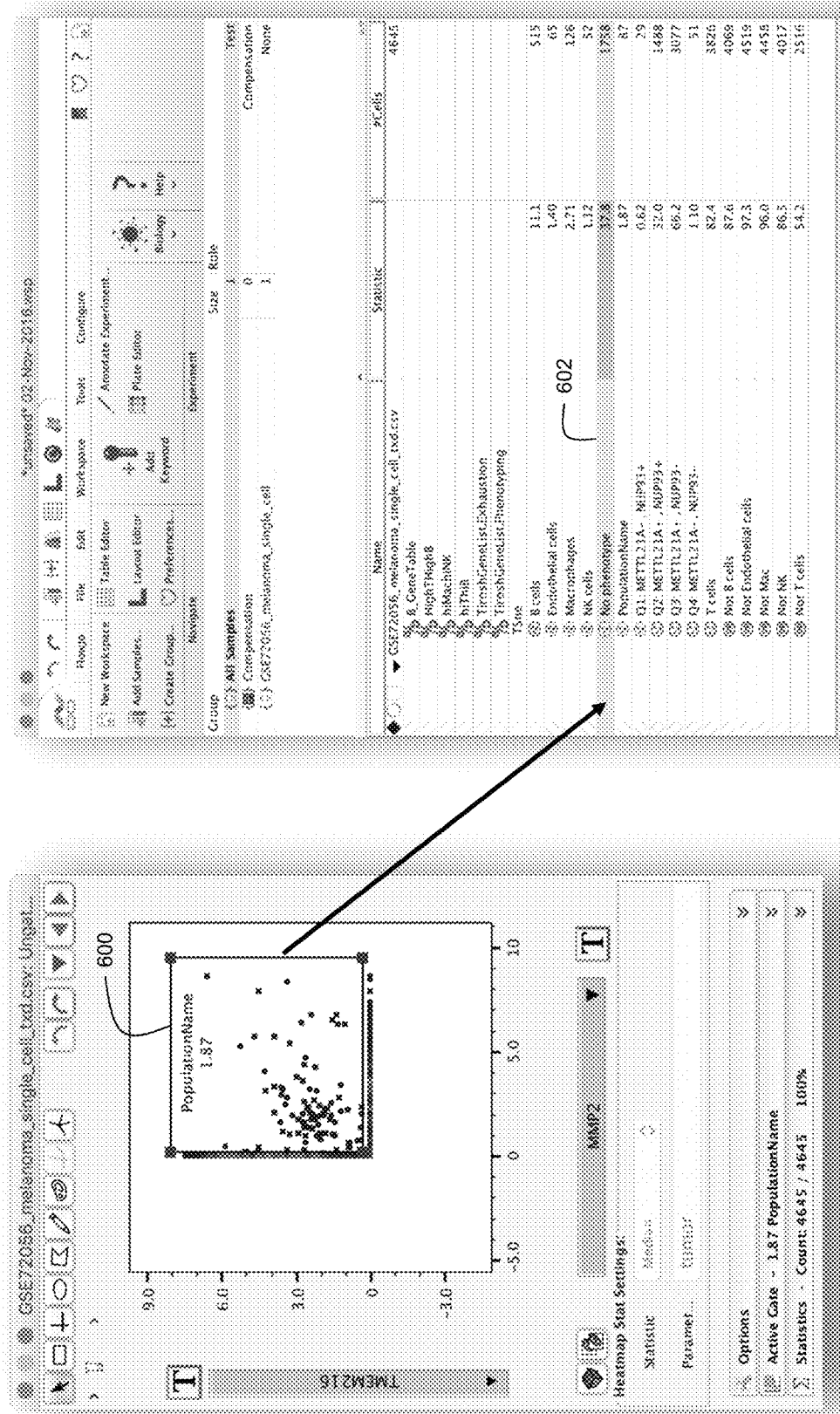
FIG. 6 shows an example of how gating can be performed within a cell view scatterplot user interface to create a cell population.

Returning to FIG. 3, a user can access gate creation tools 320 in the user interface to create a gate through which child cell populations are created. For example, the user can access a tool 320 to draw a shape in the scatterplot 300 that encompasses a subset of the cells 308. FIG. 6 depicts an example gate 600 drawn to capture the cells that have non-zero expressions of the two selected genes. The cells 308 falling inside the drawn shape 600 are gated into their own child cell population, and this cell population can be added to the workspace as a distinct object 602. To create the cell population, the processor can translate gate 600 into a plurality of boundary conditions for the gated cell population. For example, with respect to a rectangle shape as shown by gate 600, the boundary conditions can be all cells with (1) X-axis values between 1 and 10, and (2) Y-axis values between 1 and 8. The cell list data structure (e.g., the set of vectors {Cell ID 1, Gene 1 Count, Gene 2 Count}) can be traversed to find all Cell IDs meeting these criteria, and the data for these cell IDs can populate a new child cell population data structure in the workspace. Also, a corresponding scatterplot 300 of gene expressions for the child cell population can then be presented (where the cell population includes one or more cells 308). This gating can allow a user to focus on a biologically-interesting cluster of cells 308 in the scatterplot 300.

Also, the cell view mode of FIG. 3 permits users to visually compare different samples, including child and parent cell populations using navigation tools 322. For example, through the back and next buttons in tools 322, a user can navigate to a scatterplot 300 for a next and previous sample in the workspace. Through the down button in tools 322, a user can navigate to a child cell population in an analysis hierarchy (e.g., to the child cell population created via gate 600 of FIG. 6). Also, through an up button (not shown), a user can navigate to a parent cell population in the analysis hierarchy.

Figure 7:
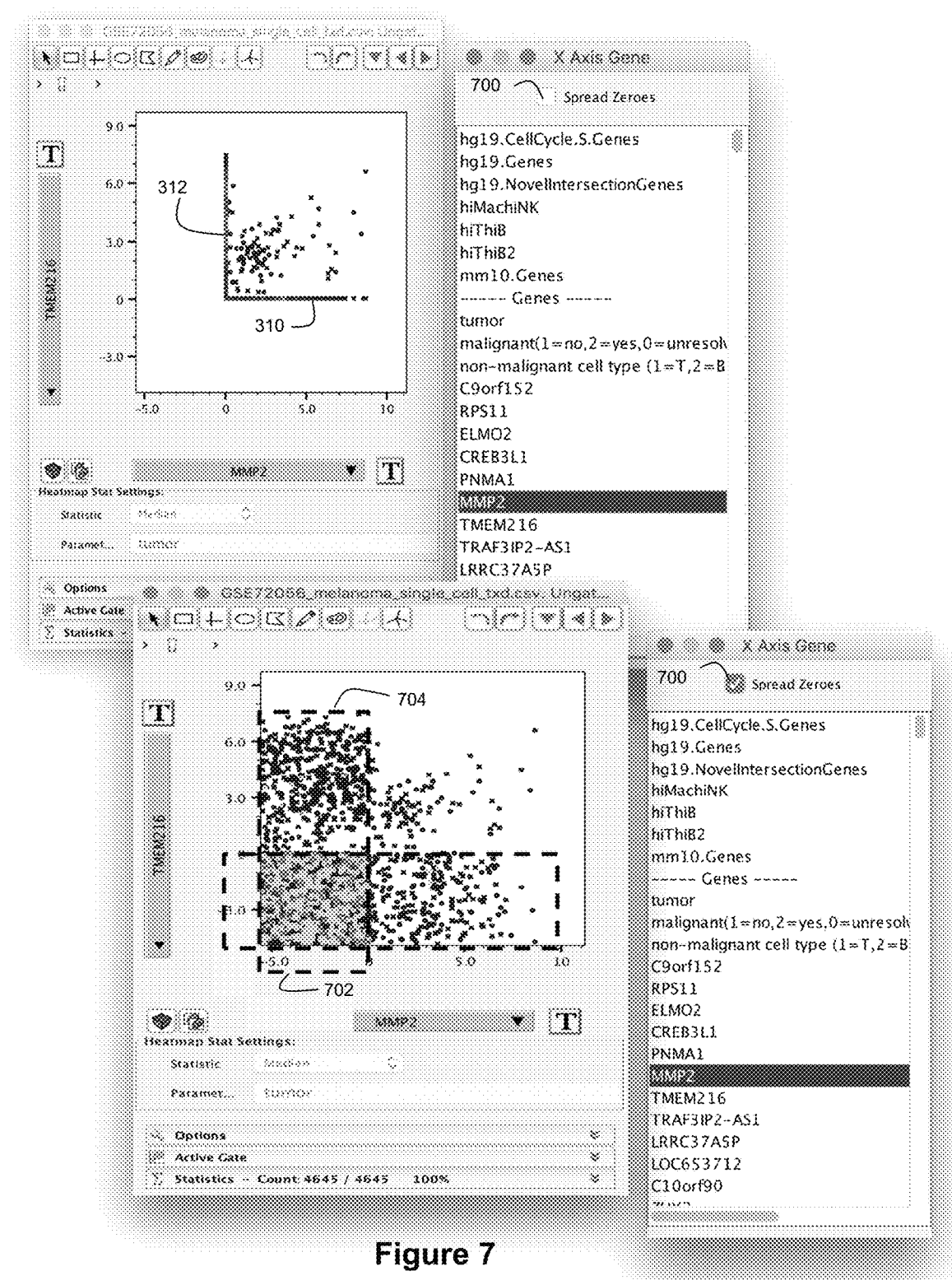
FIG. 7 shows an example user interface that permits a user to spread the zeros of a cell view scatterplot.

Furthermore, when in cell view mode, it is expected that for many cell populations there will be large numbers of cells where the expression of the selected genes for those cells is at the zero level. This leads to a large clustering of dots 308 at the zero levels 310 and 312 on the X-axis and Y-axis respectively of scatterplot 300 shown by FIG. 3. Color coding can be used at 310 and 312 to indicate the density of cells with such zero-level gene expressions. However, the inventors believe that the display can be enhanced to provide biologically-relevant information to users in certain circumstances by expanding the visualization of the zero levels for the two selected genes (or gene sets as explained below). To accomplish this, the user interface can include a "spread zeros" user control 700 (such as a check box, button, etc.) as shown in FIG. 7. This control 700 can be provided on a menu for selecting the axis parameters, although if desired by a practitioner, control 700 could be positioned elsewhere such as somewhere on the user interface shown by FIG. 3. The top half of FIG. 7 shows the scatterplot when the zeros are not spread. The bottom half of FIG. 7 shows the scatterplot when the spread zeros option is selected via input mechanism 700.

As shown by the bottom scatterplot in FIG. 7, box 702 provides an expanded view of the cells that exhibit zero values with respect to the expression of the X-axis gene (MMP2 in this example). Box 704 provides an expanded view of the cells that exhibit zero values with respect to the expression of the Y-axis gene (TMEM216 in this example). The depth of the zero space along the X and Y axes can be defined as a function of how many dots/cells are at the zero levels for each gene, and the dots/cells can be spread across the zero-space defined by boxes 702 and 704 as a function of the density of cells at each zero location, although other distribution techniques could be used. As should be understood, the lower left quadrant of the bottom scatterplot of FIG. 7 (defined by the overlap of boxes 702 and 704) comprises the cells that have zero expressions for both the X-axis and Y-axis genes. The lower right quadrant of this scatterplot comprises cells that have zero expressions of the Y-axis gene but positive expressions of the X-axis gene, and the upper left quadrant of this scatterplot comprises cells that have zero expressions of the X-axis gene but positive expressions of the Y-axis gene. The upper right quadrant of this scatterplot comprises the cells with positive expressions of both genes (effectively, the scatterplot shown in the top part of FIG. 7). As can be seen from the bottom scatterplot of FIG. 7, the cell population of the upper right quadrant is much sparser than the other quadrants. The inventors believe that the ability to visualize the zero levels in this spread manner can provide users with biologically relevant information (such as an ability to assess gene combinations where unexpected distributions occur—e.g., where the upper right quadrant is not as sparse as would be generally expected).

Figure 8:
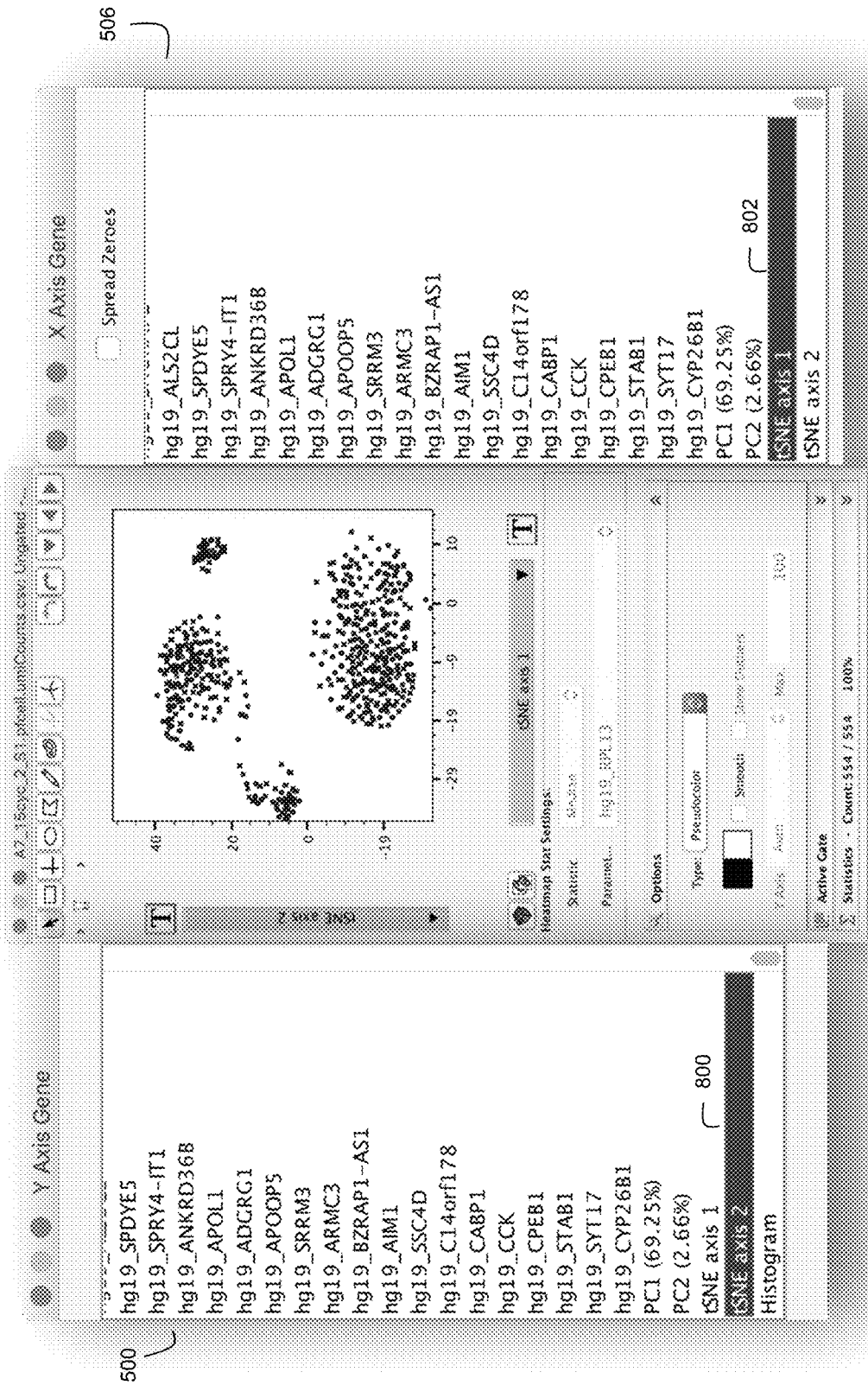
FIG. 8 shows an example cell view scatterplot where parameters other than genes are selected as axis parameters.
Figure 9:
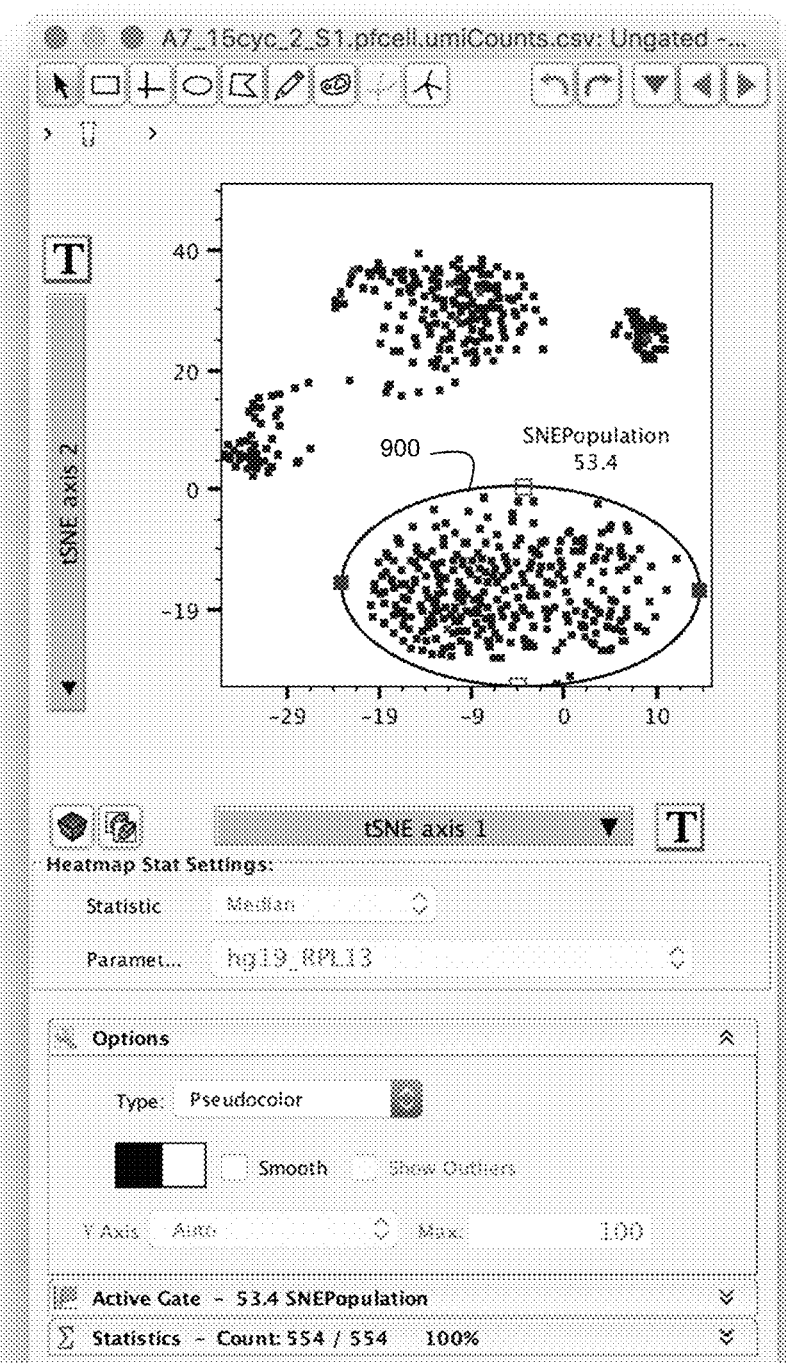
FIG. 9 shows an example of how gating can be performed within the cell view scatterplot of FIG. 8 to create a cell population.

The cell view scatterplot can also display cell information for selected parameters in the cellular gene expression data 112 other than genes. As indicated above, the cellular gene expression data 112 may include parameters from dimensionality reduction such as those resulting from tSNE, LDA, PCA, etc. and quality control parameters (above threshold, parameters relating to ribosomal RNA (rRNA) abundance, etc.) These parameters can be presented as options on the parameter selection menus 500 and 506. FIG. 8 shows an example where selection 800 for the Y-axis is the parameter tSNE axis 2 and where selection 02 for the X-axis is the parameter tSNE axis 1. The resultant scatterplot of FIG. 8 can be created via the FIG. 4 process flow. A user can also gate desired cell populations in the scatterplot of FIG. 8 (see gate 900 in FIG. 9) as explained above with respect to FIG. 6.

Figure 10:
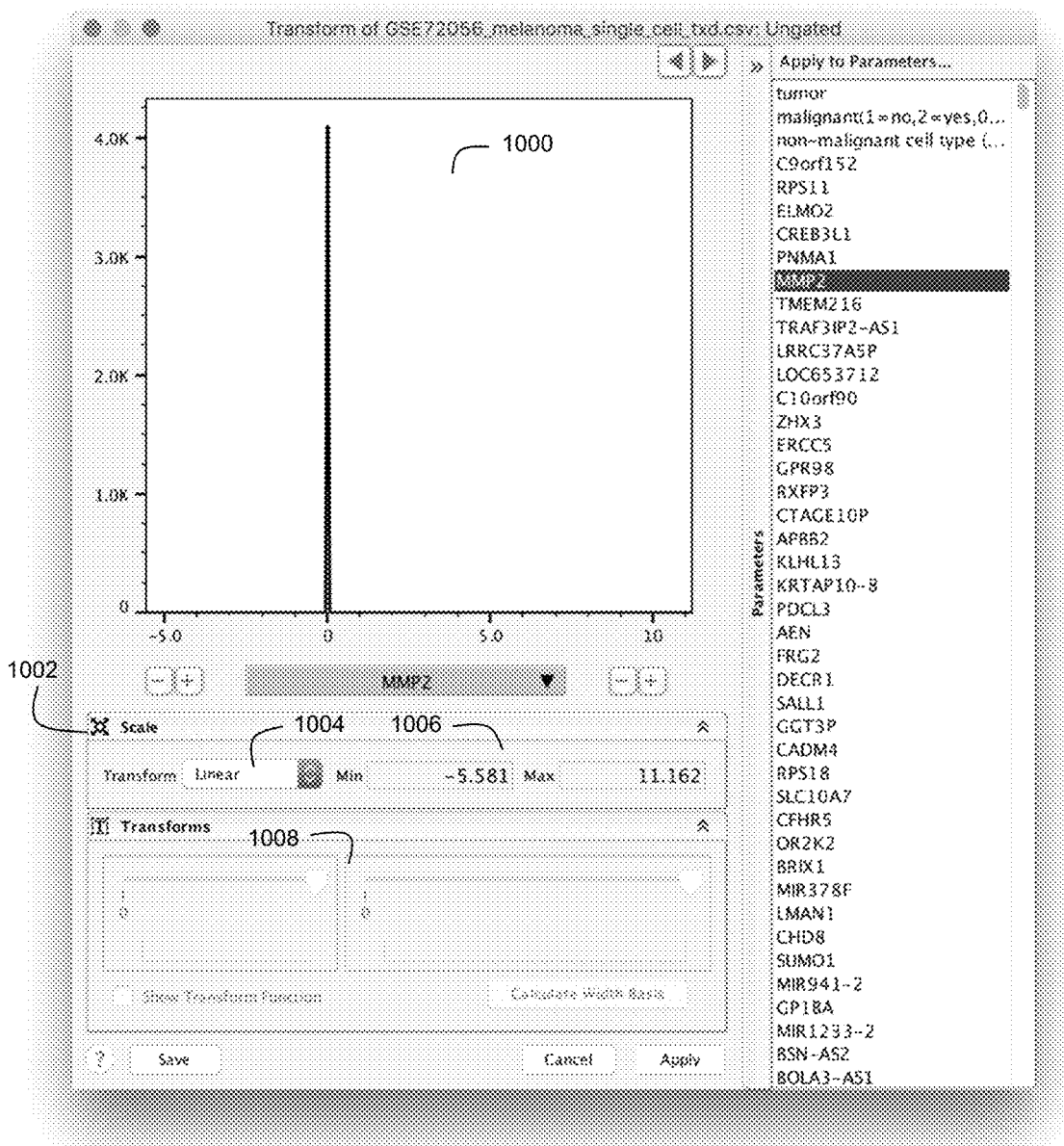
FIG. 10 shows an example user interface for adjusting display settings in a scatterplot presentation.

The cell view user interface of FIG. 3 can also include a user control 330 (e.g., the "T" button of FIG. 3) through which the user can alter the display of information in scatterplot 300. Upon selection of T button 330, the user interface of FIG. 10 can be presented. Through this interface, a user can change the binning/display of scatterplot data interactively and live. The list at right in FIG. 10 shows the available and selected parameters for the X-axis of the scatterplot. A histogram 1000 shows the binning of values for the selected parameter with respect to the subject cell population. Given the high prevalence of zeros, histogram 1000 shows a large spike at the zero level, and the scale of this example obscures the non-zero levels in the histogram. Through left/right arrows shown toward the top of FIG. 10, a user can quickly preview displays for different samples. Through +/− controls in the middle of FIG. 10, a user can easily alter the histogram zoom level.

Through scale controls 1002, the user can adjust the X-axis of the scatterplot in a variety of ways. For example, the X-axis scale can be defined to exhibit a liner scale or some other scale (such as a log 2 scale) (see control 1004). Also, through min/max controls 1006, the user can define the minimum and maximum boundaries on the X-axis. For example, through these controls, the minimum value can be defined to be a value greater than zero, which would remove the zero spike from the histogram and re-present a newly scaled histogram where the distribution of non-zero values across the X-axis can be more clearly seen. Sliders 1008 can provide users with easy control over the transformation variables. Also, it should be understood that additional transformation options can be provided, including user-supplied transforms whose variables can be adjusted by user input (see, e.g., US Pat App Pub 2016/0328249 entitled "Plugin Interface and Framework for Integrating External Algorithms with Sample Data Analysis Software", the entire disclosure of which is incorporated herein by reference).

Figure 11:
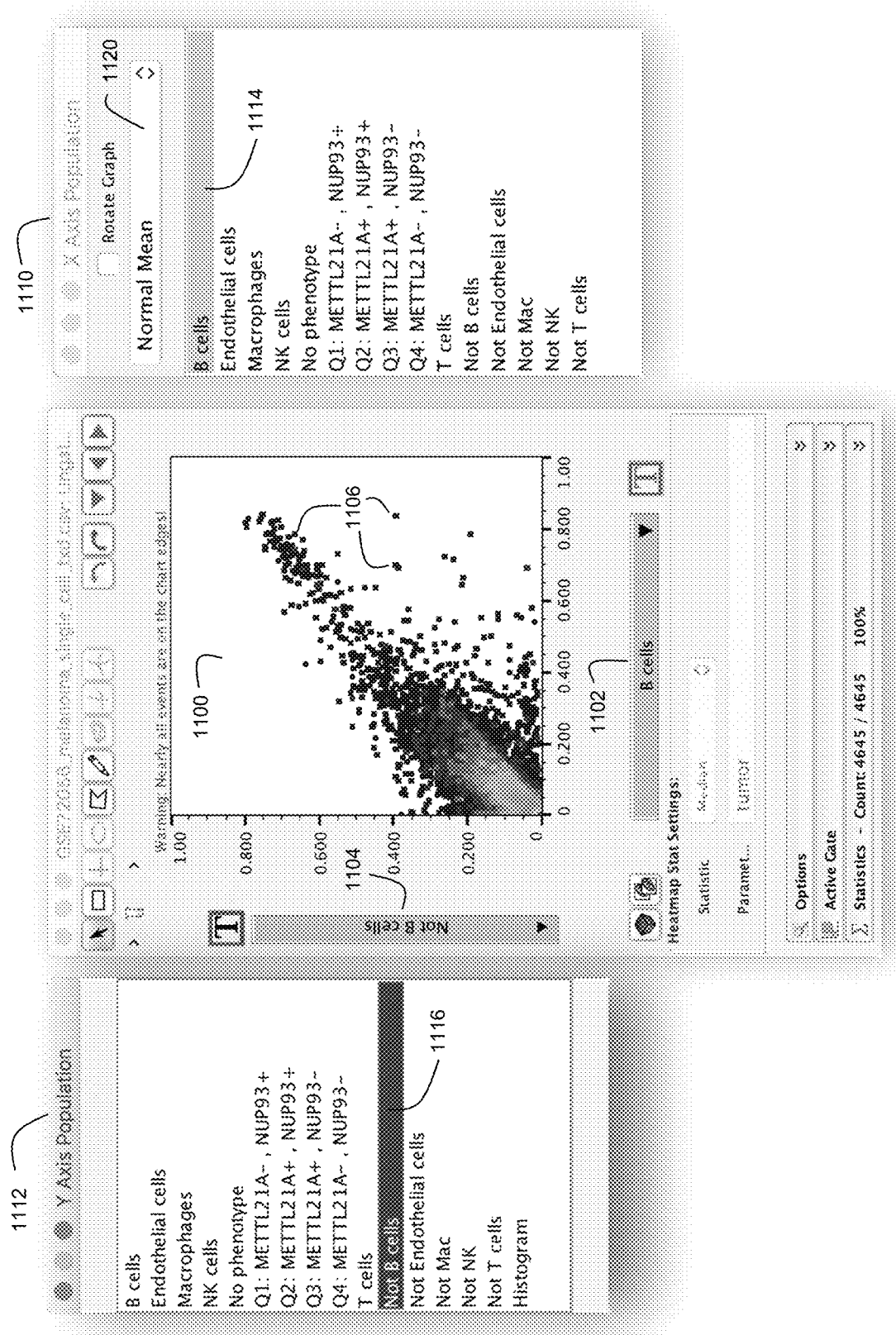
FIG. 11 depicts an example gene view graph window scatterplot including cell population selection menus.

A particularly innovative and powerful aspect of the inventive system disclosed herein is the ability to pivot the scatterplot display from a cell view mode to a gene view mode. FIG. 11 shows an example of a scatterplot 1100 in the gene view mode. As used herein, a "gene view" visualization refers to a visualization where genes are the individual data points measured against the axis dimensions (e.g., genes as the dots in a scatterplot measured against two cell populations). With scatterplot 1100, the axis parameters are cell populations (see the X-axis parameter 1102 which identifies a population of B cells, and the Y-axis parameter 1104 which identifies a population of "not B" cells in this example). The dots 1106 in scatterplot 1106 represent specific genes (rather than individual cells as in scatterplot 300 of FIG. 3). Population selection menu 1110 provides a list of cell populations available for selection to be used on the X-axis, and population selection menu 1112 provides a list of cell populations available for selection to be used on the Y-axis. As noted, in this example, selections 1114 and 1116 correspond to populations of B cells and "not B" cells respectively.

With this pivot, with reference to cellular gene expression data 112 such as table 200 from FIG. 2, the table 200 can be pivoted such the genes become rows in the table and subsets of the cells are grouped into two cell populations that become the columns of the tables. Furthermore, computations can be performed on the gene counts in table 2 for the cells of the two cell populations to determine the values that will populate the cells of the pivoted table. Through control 1120 of FIG. 11, a user can define the computations that are to be performed on the gene data to compute the values for the cells in the pivoted table. In the example of FIG. 11, a normalized mean computation has been selected. However, it should be understood that other computational options can be available, such as normalized medians, normalized modes, straight means, straight medians, straight modes, etc. Accordingly, it should be understood that the computation performed on the pivoted table data can be any user-defined function that is deemed biologically-relevant to a user. The inventors note that it may be desirable for the computation to be based on averaging of some sort to account for potential discrepancies in the cell counts of the two cell populations and/or normalization to account for the variability between samples (e.g. normalization to a spike-in of External RNA Controls Consortium (ERCC) controls which contain a known amount of RNA to be measured). For example, if the pivoted table values were straight counts of each gene in the two cell populations, and if there was a meaningful difference in the count of cells in the two cell populations, the aggregated gene count totals across the two cell populations would not be very informative in a comparative sense. However, if the cell populations were roughly similar in size, straight gene counts for each gene in the two cell populations might nevertheless be informative.

Figure 12:
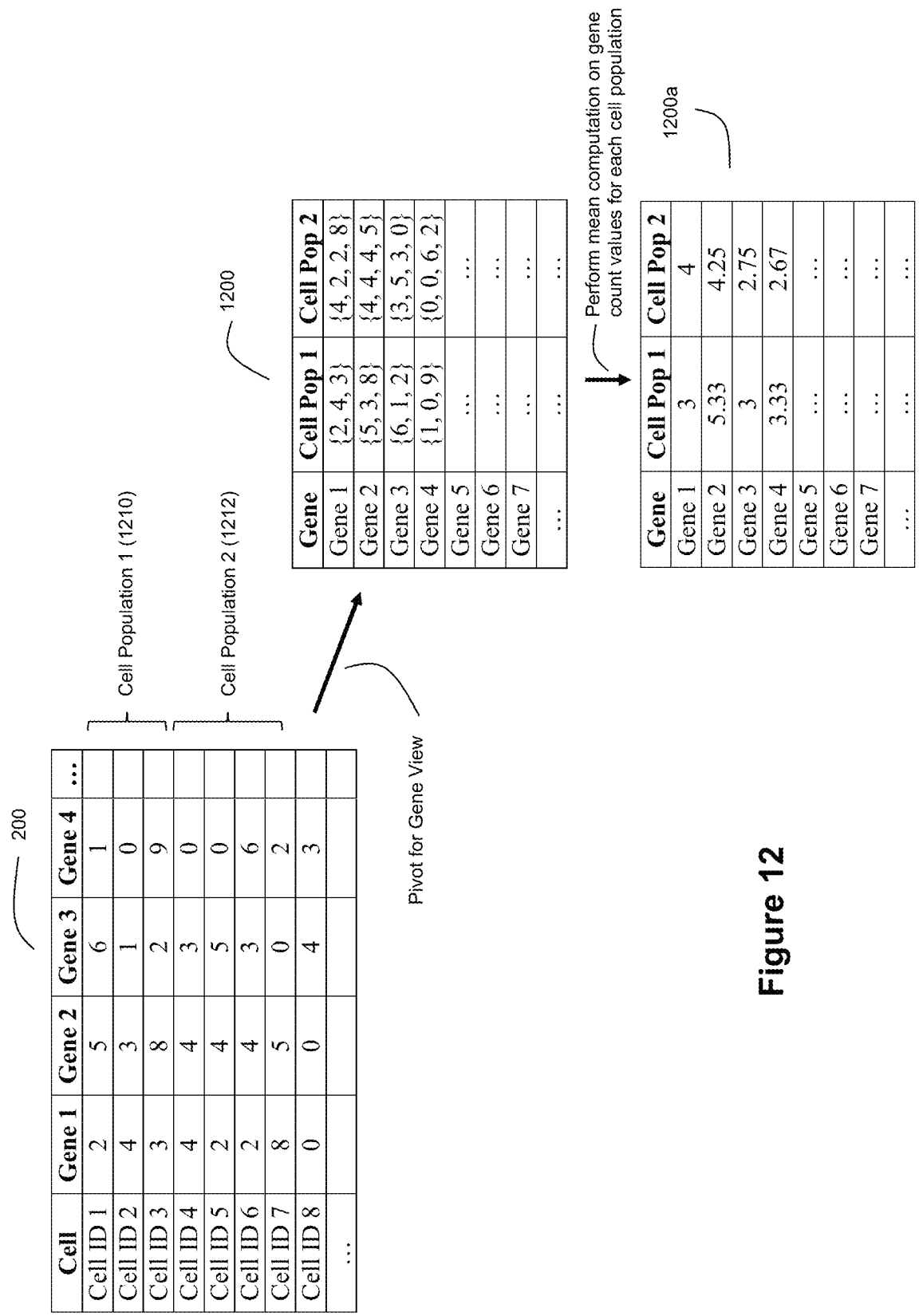
FIG. 12 depicts an example of how cellular gene expression data can be pivoted to create cell population data for a gene view scatterplot.

FIG. 12 depicts an example pivot from a cell view to a gene view. Table 200 in FIG. 12 shows gene expressions per cell for a number of cells in a sample. Each row corresponds to a different cell, and the columns correspond to expression counts for different genes in the associated cells. If subsets of these cells are grouped into two cell populations 1210 and 1212 as shown in FIG. 12 (e.g., via gating in the cell view scatterplot 300), these two cell populations can be pivoted as shown to create the pivoted table 1200. In pivoted table 1200, the rows are the genes that were columns in table 200. The columns in table 1200 are the two cell populations 1210 and 1212. Each table cell is populated with a concatenation of the gene counts for the associated gene in the cells of each cell population. In the example of FIG. 12, the computation being performed on these values is a straight averaging to compute means as shown in pivoted table 1200a. Once again, as noted above, it should be understood that other computations could be performed if desired by a practitioner. A gene view scatterplot of the type shown by scatterplot 1100 in FIG. 11 can then be created from pivoted table 1200a using the same basic techniques described in FIG. 4 (albeit using pivoted table 1200a rather than table 200).

Returning to FIG. 11, the gene view scatterplot 1100 thus provides users with a powerful manner of visualizing differential gene expression between two cell populations over a list of genes that may be extremely large in size. The inventors believe that scatterplot 1100 represents a pioneering new way of visualizing cellular gene expression data in a manner that opens up a wide new array of investigatory options for practitioners, some examples of which are described below. The example gene view scatterplot 1100 of FIG. 11 provides users with flexibility in specifying the x/y axis populations and dynamically updating gene expression graphs as populations change. The example gene view scatterplot 1100 also provides users with a plethora of graph options and resolutions. Importantly, the analysis does not stop with this graph; it continues with the ability to create new gene sets and dig deeper into the data as discussed below. Examining cellular heterogeneity and differences between samples/patients revealed by particularly new single cell methods is not possible without this approach.

The diagonal where y=x is where genes 1106 are positioned if those genes are equally expressed in both cell populations according to the metric defined via 1120. Thus, the distance of a gene 1106 away from this diagonal in either direction indicates the extent of differential expression of the subject gene 1106 as between two selected cell populations. Given that it is expected that most genes 1106 will not be expressed (or will be only lightly expressed) in many cell populations, it is expected that there will typically be large cluster of genes 1106 in the lower left quadrant of scatterplot 1100.

Figure 13A:
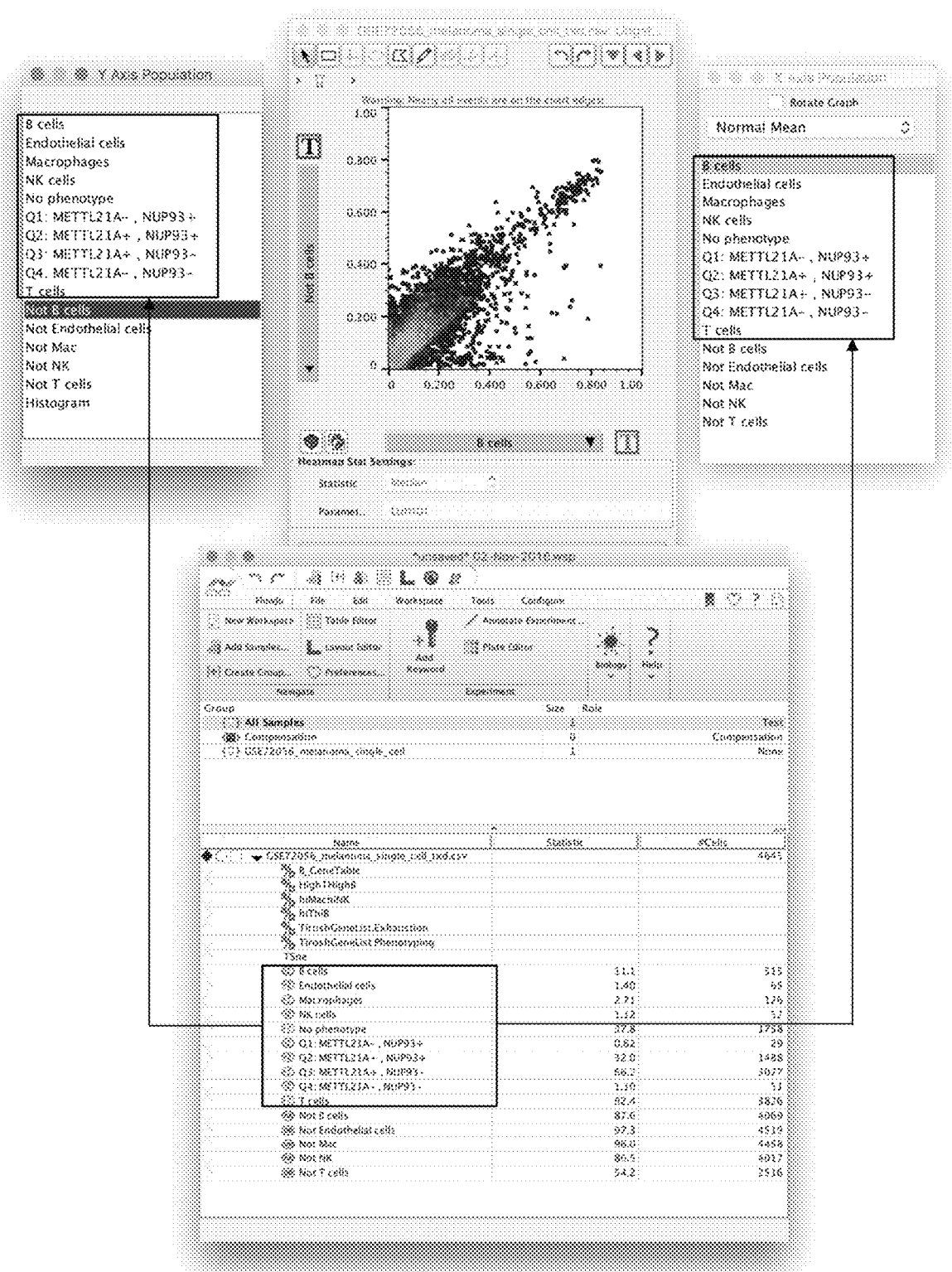
FIGS. 13A and B depict examples of how complementary cell populations can be created and defined in a workspace for use in gene view scatterplots.
Figure 13B:
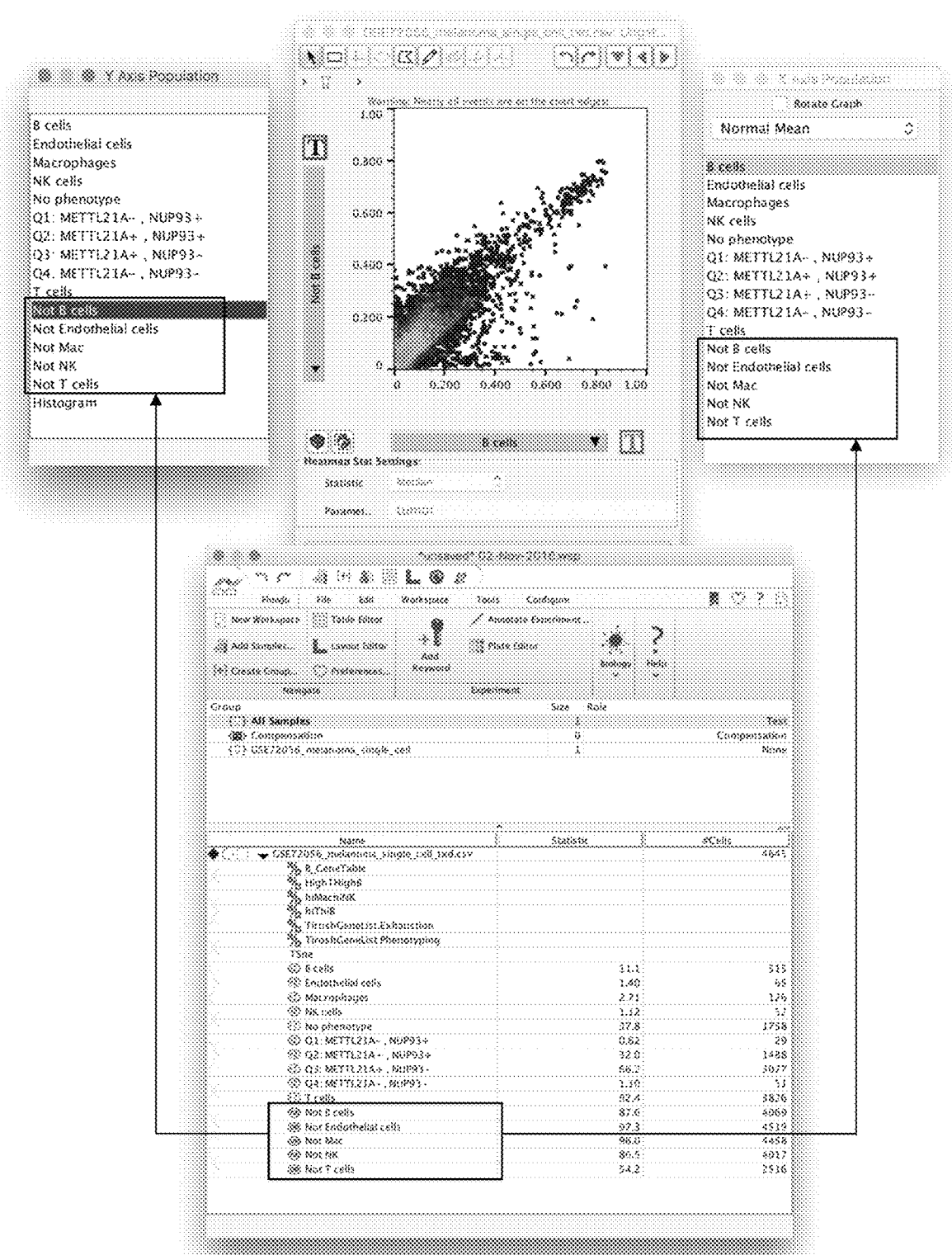

Furthermore, since users can create multiple, hierarchically-related cell populations that exist as data objects in the workspace as described in connection with FIG. 6, the user can select any of these cell populations while in the gene view mode. Furthermore, it should be understood that the workspace can be used to create Boolean expressions of cell populations (e.g., the OR combination of all cell populations that are "Not B Cells" to create complementary cell populations) for exploration in the gene view mode. FIGS. 13A and B show examples of such complementary Boolean cell populations in a workspace. Accordingly, a user can create a scatterplot 1100 that shows differential gene expression as between a population of B cells and a population of "not B" cells.

Figure 14:
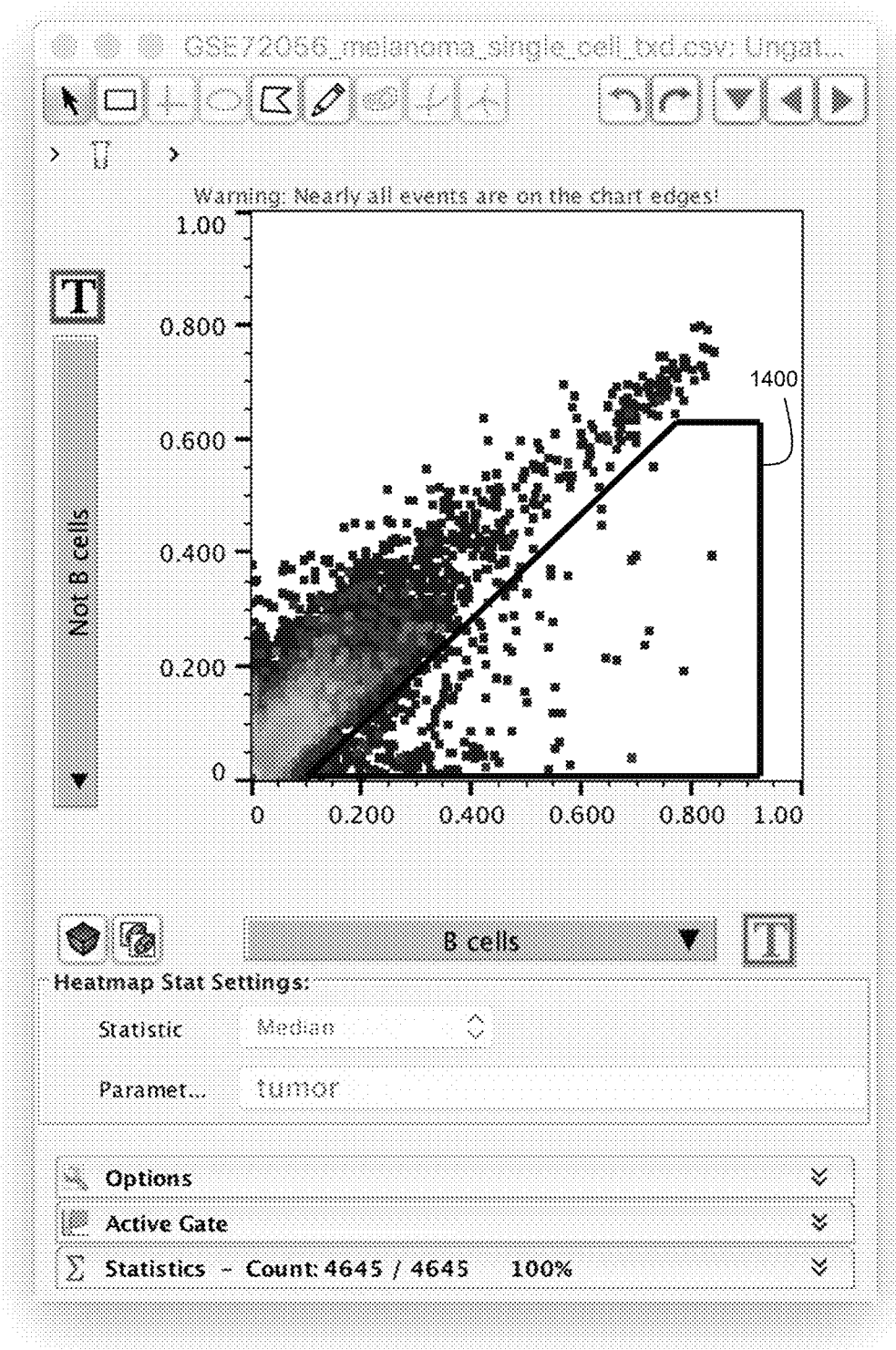
FIG. 14 shows an example of how gating can be performed within a gene view scatterplot user interface to create a gene set.

Another powerful and innovative aspect of the gene view mode described herein is an ability for users to gate genes while in the gene view mode to thereby create gene sets. FIG. 14 shows an example where gate 1400 is created in the gene view scatterplot to capture a set of genes that the user deems worthy of further investigation. Gate 1400 can be drawn on the scatterplot using the techniques described above in connection with FIG. 6. This gating will create a data structure in the workspace corresponding to the gene set defined by gate 1400 (where the gene set comprises one or more genes depending on how many genes 1106 are encompassed by the user-defined gate 1400). Such a gene set can then serve as a synthetic parameter in relation to the cellular gene expression data 112 that can be selected for visualization while in the cell view mode. In the example of FIG. 14, gate 1400 is a trapezoidal shape that captures the genes 1106 that have a positive differential expression in B cells versus non-B cells. The extent of the positive differential expression is controlled by the user through the distance of the trapezoid's diagonal line away from the y=x diagonal of the scatterplot.

Figure 15:
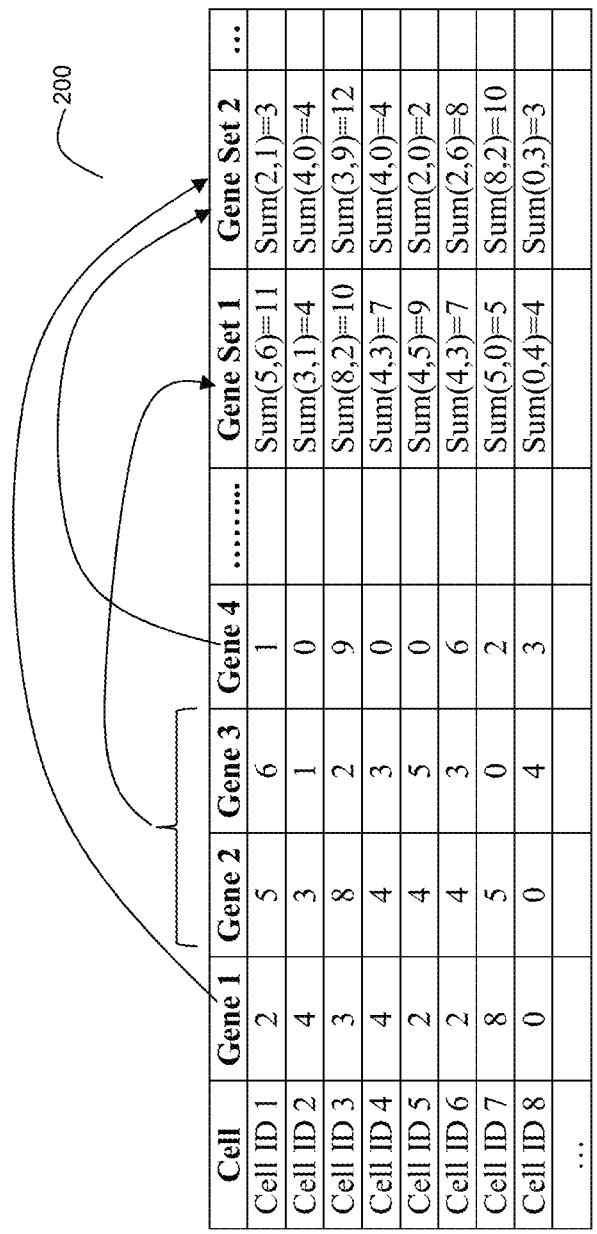
FIG. 15 shows an example of how cellular gene expression data can be augmented with gene sets as synthetic parameters.
Figure 16:
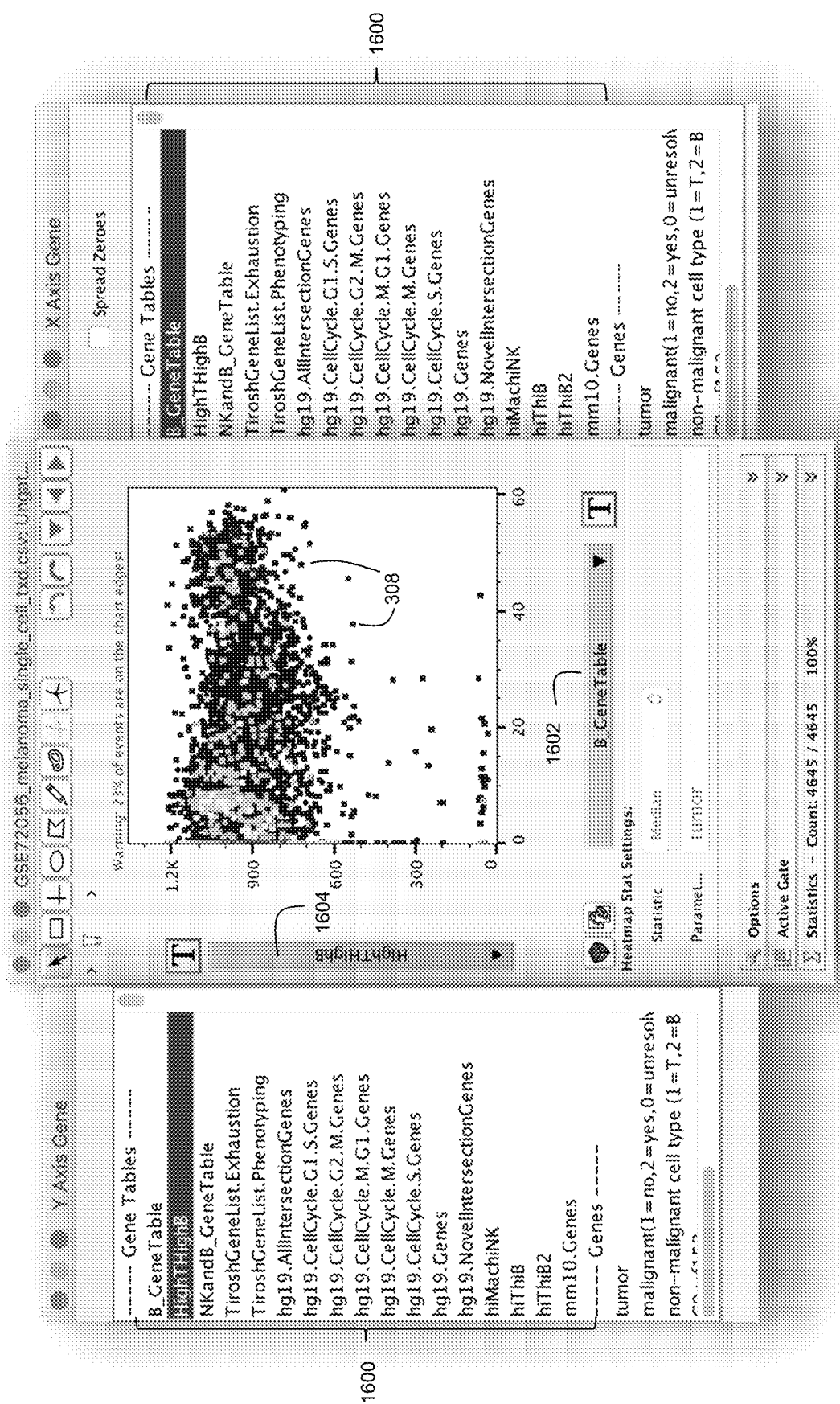
FIG. 16 shows an example of a cell view scatterplot where gene sets are presented as options in the parameter selection menus.

FIG. 15 shows an example of how the cellular gene expression data 112 can be augmented with gene sets as a synthetic parameter (in the form of example augmented table 200). This table 200 has been augmented with two gene sets as parameters (see the Gene Set 1 and Gene Set 2 columns). In this example, Gene Set 1 consists of {Gene 2, Gene 3} and Gene Set 2 consists of {Gene 1, Gene 4}. The table cells for these gene sets (each corresponding to a different cell in the table rows) can then be populated with the sums of the gene counts for the constituent genes of the subject gene sets. Accordingly, a user can return to the cell view mode to create a cell view scatterplot where one or both of the X-axis and Y-axis parameters are gene sets. An example of this is shown by FIG. 16. The parameter selection menus for each axis in FIG. 16 include a section that lists available gene set options. The cell view scatterplot of FIG. 16 thus shows a scatterplot of cells 308 where the X-axis parameter is the gene set labeled "B_GeneTable" and the Y-axis parameter is the gene set labeled "HighTHighB". Thus, it should be understood that the gating capabilities within the gene view scatterplot to create gene sets in combination with the ability use the created gene sets as a synthetic parameter used in a cell view scatterplot provide users with unprecedented capabilities for intelligently reducing the multi-parameter data space of cellular gene expression data. This combination allows the user to overcome the extremely difficult problem of identifying common genes in populations and identifying the differential genes in populations. In other words, whether the user is looking for what genes are in common, or which genes are different, the ability to create new gene sets and viewing/analyzing them as a single parameter allows the user to focus on the important relationships between cell populations and gene sets. Furthermore, as users create gene sets of biological interest based on various comparisons of cell populations, these gene sets can be shared with other users by passing these gene sets (as a defined list of encompassed genes) to other users so that those other uses can evaluate the gene sets with their samples of cell data. Based on such sharing and independent investigation across different cellular data sets, it is expected that greater insights into gene behavior with respect to cells can be gained.

Figure 17A:
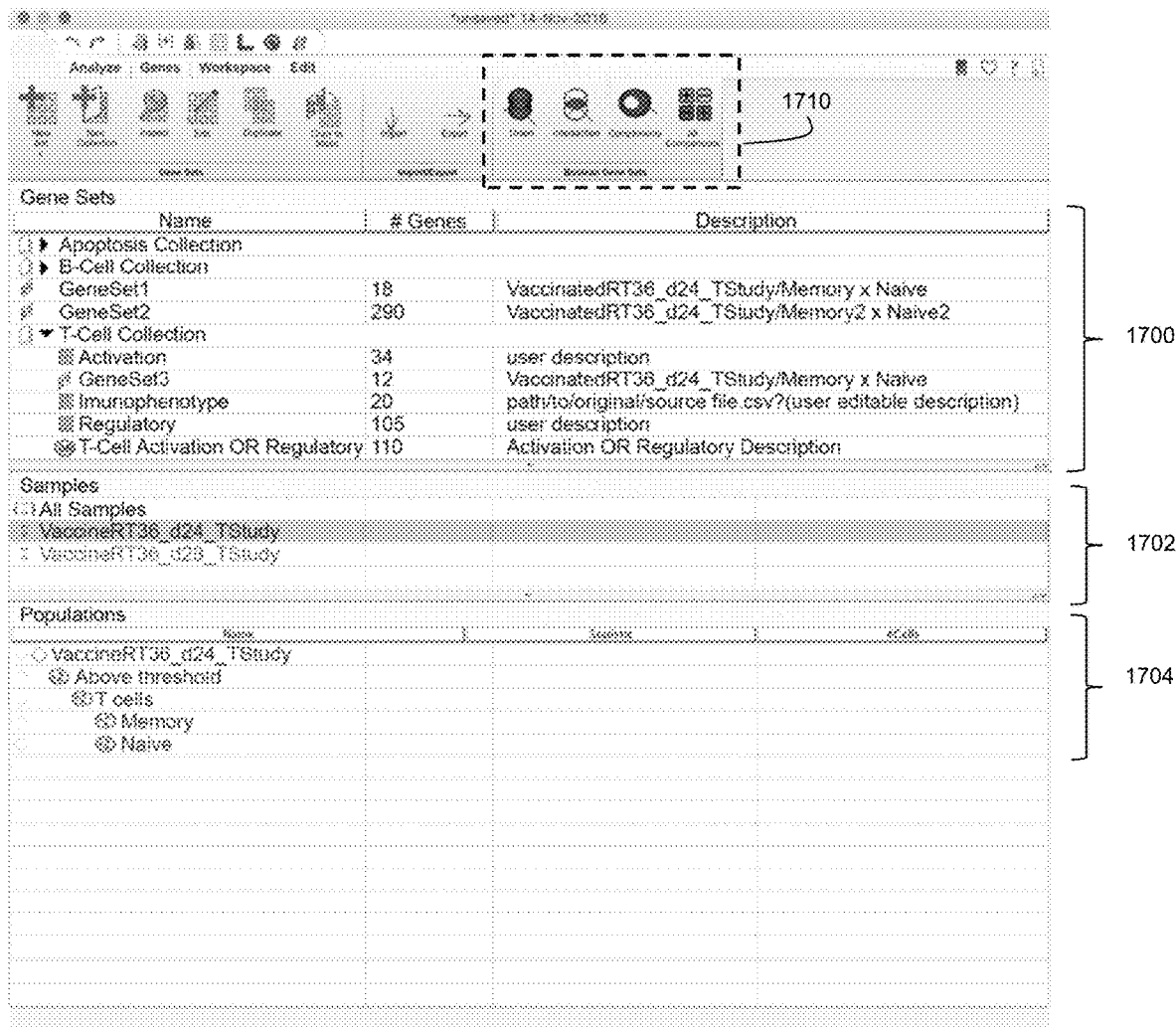
FIGS. 17A and B show an example user interface for viewing, editing, and creating new gene sets from other gene sets in a workspace.

FIG. 17A shows an example view into a workspace that breaks the workspace down into various gene sets 1700, samples 1702, and cell populations 1704 that exist within the workspace. As shown, the section 1700 that lists gene sets can include various display fields that provide metadata about each subject gene set (e.g., a name, count of genes within the gene set, and a description of the gene set). The name and description can be editable by a user and will be helpful for informing users about pertinent characteristics of the gene set. Also, the gene sets can be listed in a manner that indicates any hierarchical relationships that exist within gene sets.

Figure 17B:
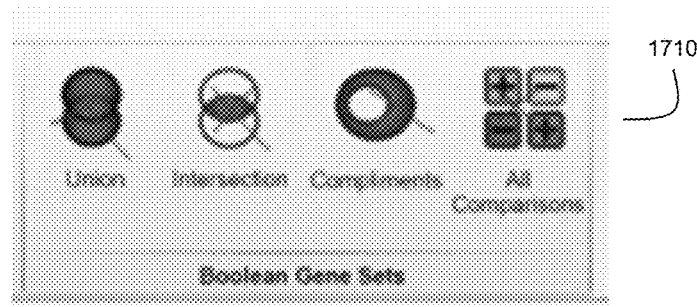

Gene set controls 1710 (shown in greater detail in FIG. 17B) provide a user with an ability to create gene sets from other gene sets via Boolean operations. For example, via the union button, a user can create a new gene set that is the union of two or more selected gene sets within list 1700. Via the intersection button, a user can create a new gene set that consists of the genes that are present in both/all of two or more selected gene sets within list 1700. Via the complement button, a user can create a complementary gene set from two gene sets (Gene Set 1 and Gene Set 2) within list 1700 where a first complementary new gene set consists of all of the genes that are in Gene Set 1 but not Gene Set 2 and where a second complementary new gene set consists of all of the genes that are in Gene Set 2 but not Gene Set 1. Via the "All Comparisons" button, a user can create several new gene sets at the same time via each of the techniques described above (new gene sets via the union operation, the intersection operation, and the complementary operation). This flexible ability to create new gene sets from existing gene sets allows for the comparison of gene sets between treatment conditions, patients, experiments, etc. Accordingly, by using controls 1710, a user can create gene collections that comprise combinations of gene sets.

Figures 18A, 18B:
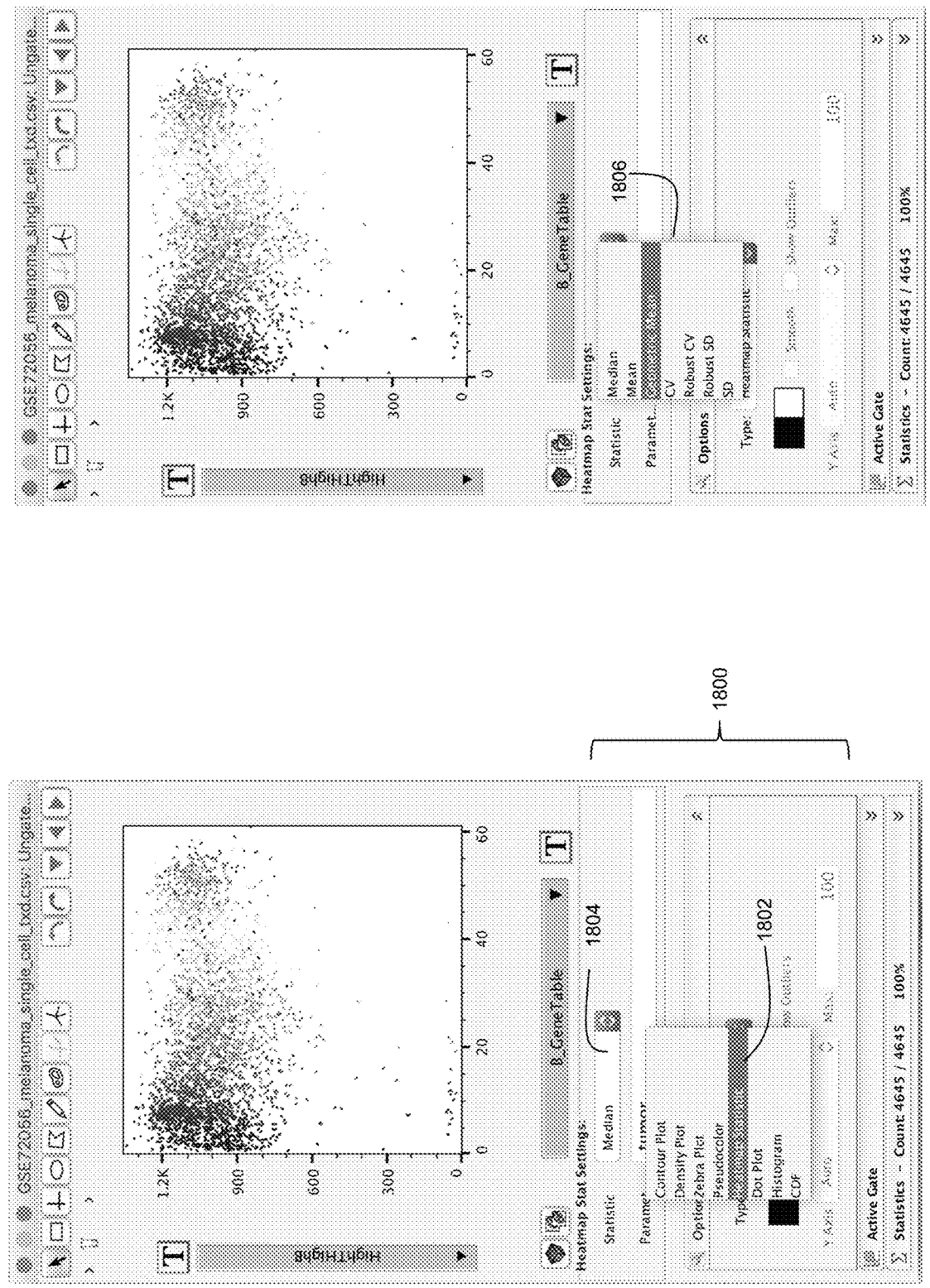
FIG. 18A-D show examples of how a user-selected third dimension can be overlaid on a scatterplot.

Another powerful and innovative aspect of the visualizations provided by program 116 include an ability to overlap a third dimension on the cell view and/or gene view scatterplots. For example, color coding (e.g., a heatmap) can be applied to the cells 308 or genes 1106 in a scatterplot to provide another dimension to the data presentation. An example of this is shown by FIGS. 18A-D. FIG. 18A shows how third dimension controls 1800 can be used to define how the third dimension is presented within an example cell view scatterplot display (e.g., as a heatmap statistic). Through control 1804, the user can define the statistic to be used for the heatmap. FIG. 18B shows the options that are available for this statistic 1804 in an example embodiment (e.g., median, mean, geometric mean, coefficient of variation (CV), robust CV, standard deviation (SD), robust SD, etc.). A heatmap statistic can be calculated as follows: Each dot in the graph represents one or more cells (usually multiple cells). For each dot, the selected statistic (e.g., mean, median, etc) is calculated for the cell(s). Thus if there are 400 dots in the graph, then 400 statistical values are calculated. For the 400 statistical values, the min and max are determined, and are used as the lower and upper bound to index into a color map (an array of color values whose gradient changes from one color to another) i.e the min value is mapped to index 0 in the color array, and the max value is mapped to the last index in the color map. Colors in the color map can then be applied to values between the min and max values in some fashion (such as a linear distribution of colors to values).

Figures 18C, 18D:
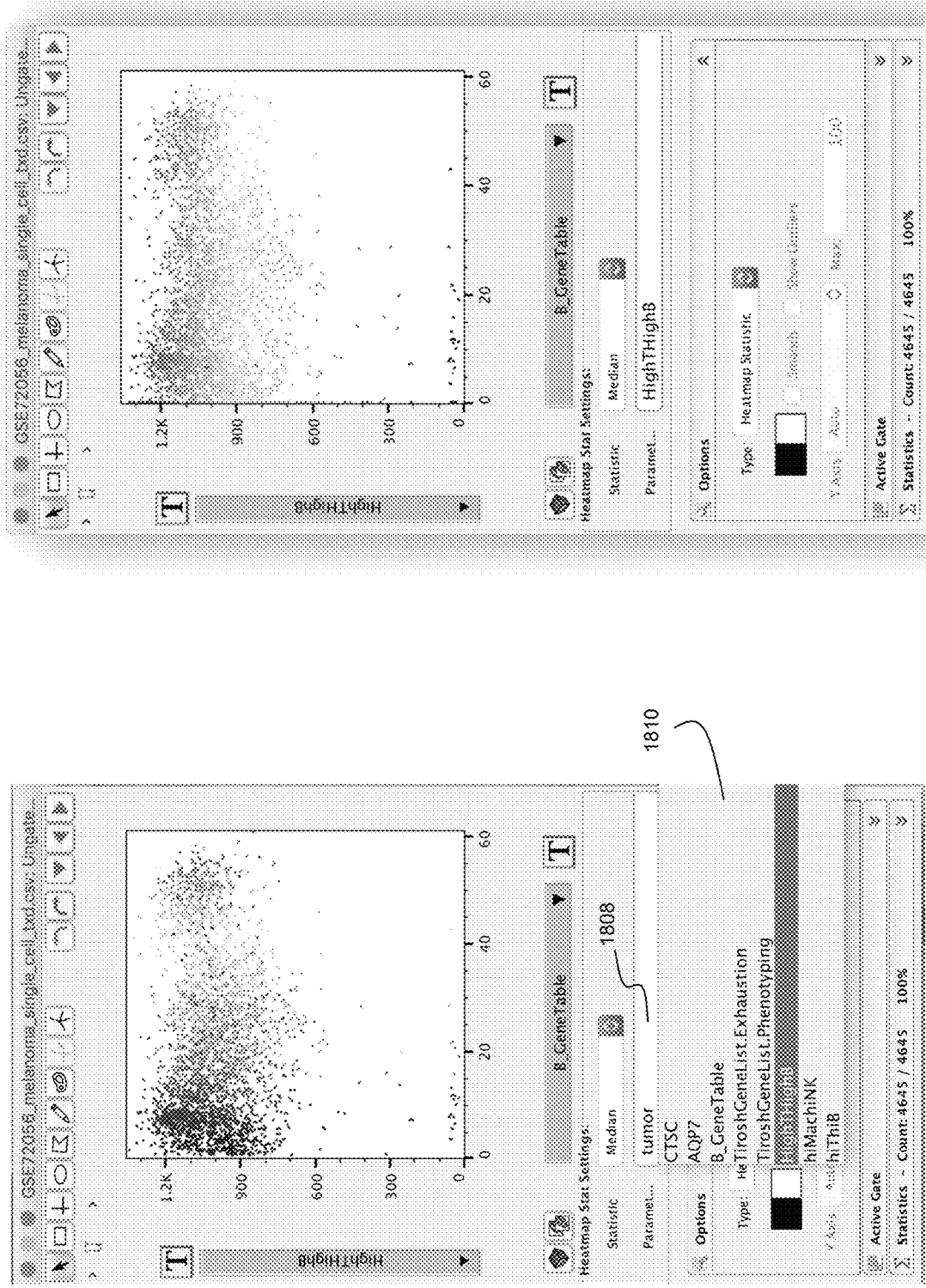
Figure 19:
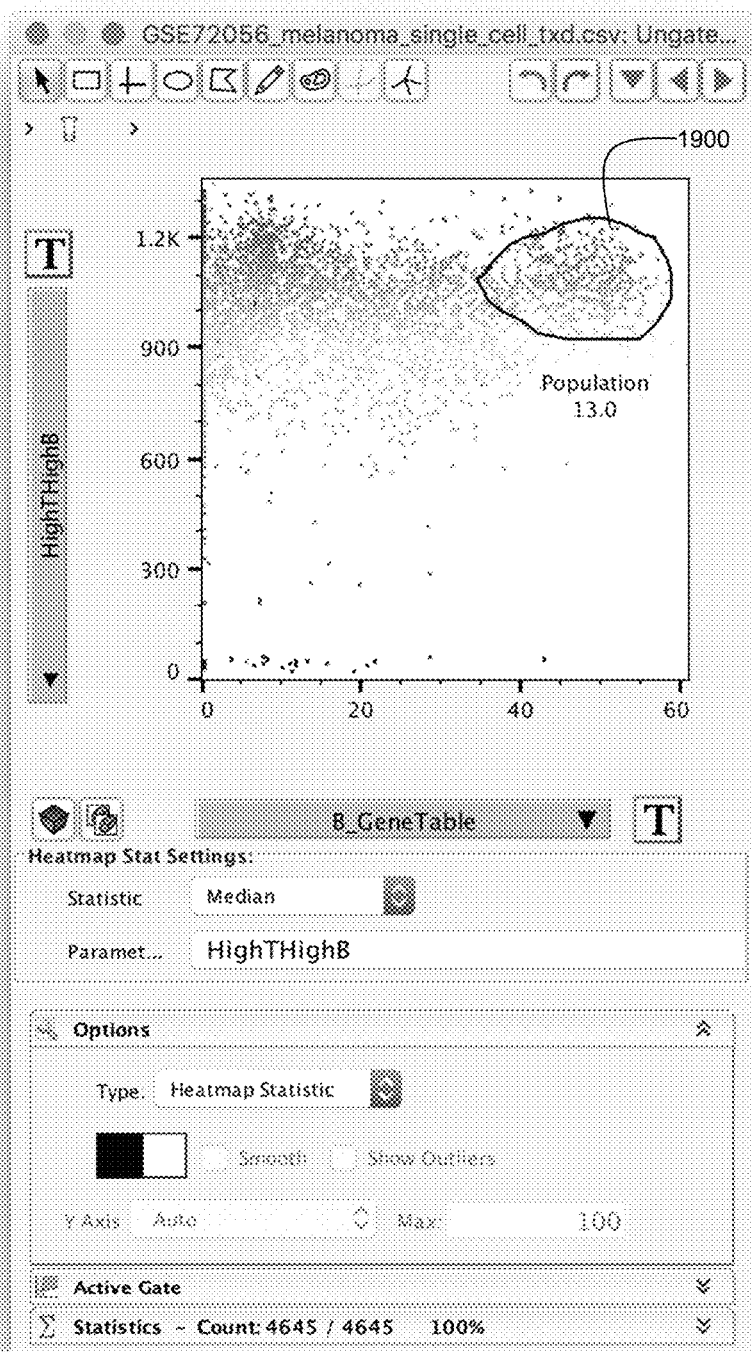
FIG. 19 shows an example of how gating can be performed within the 3D scatterplots of FIGS. 18A-D.

FIG. 18C shows how a user can select a parameter 1808 from the cellular gene expression data for use as the third dimension. Parameter list 1810 can be populated with a list of the parameters for the cellular gene expression data (e.g., the columns in table 200). In this example, the user has selected the parameter HighTHighB as a third dimension to be overlayed via color coding on the cell view scatterplot, as shown by FIG. 18D. This third dimension overlay provides a user with a further capability for meaningfully interpreting a scatterplot. For example, the user can use the color coding to identify cell populations of interest and gate such cell populations (see gate 1900 in FIG. 19), thereby creating another new object in the workspace as a cell population for further investigation.

Figure 20A:
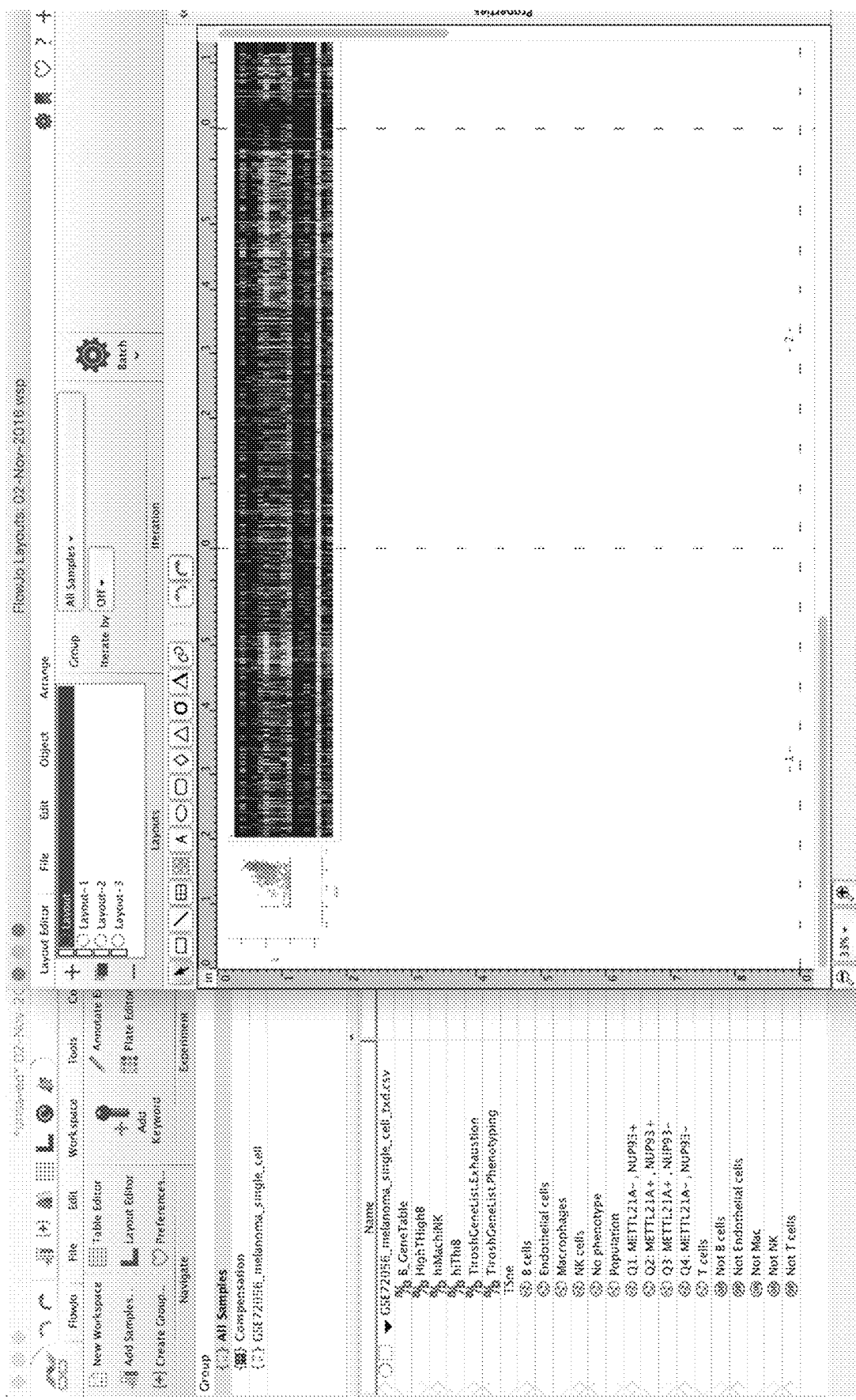
Figure 20D:
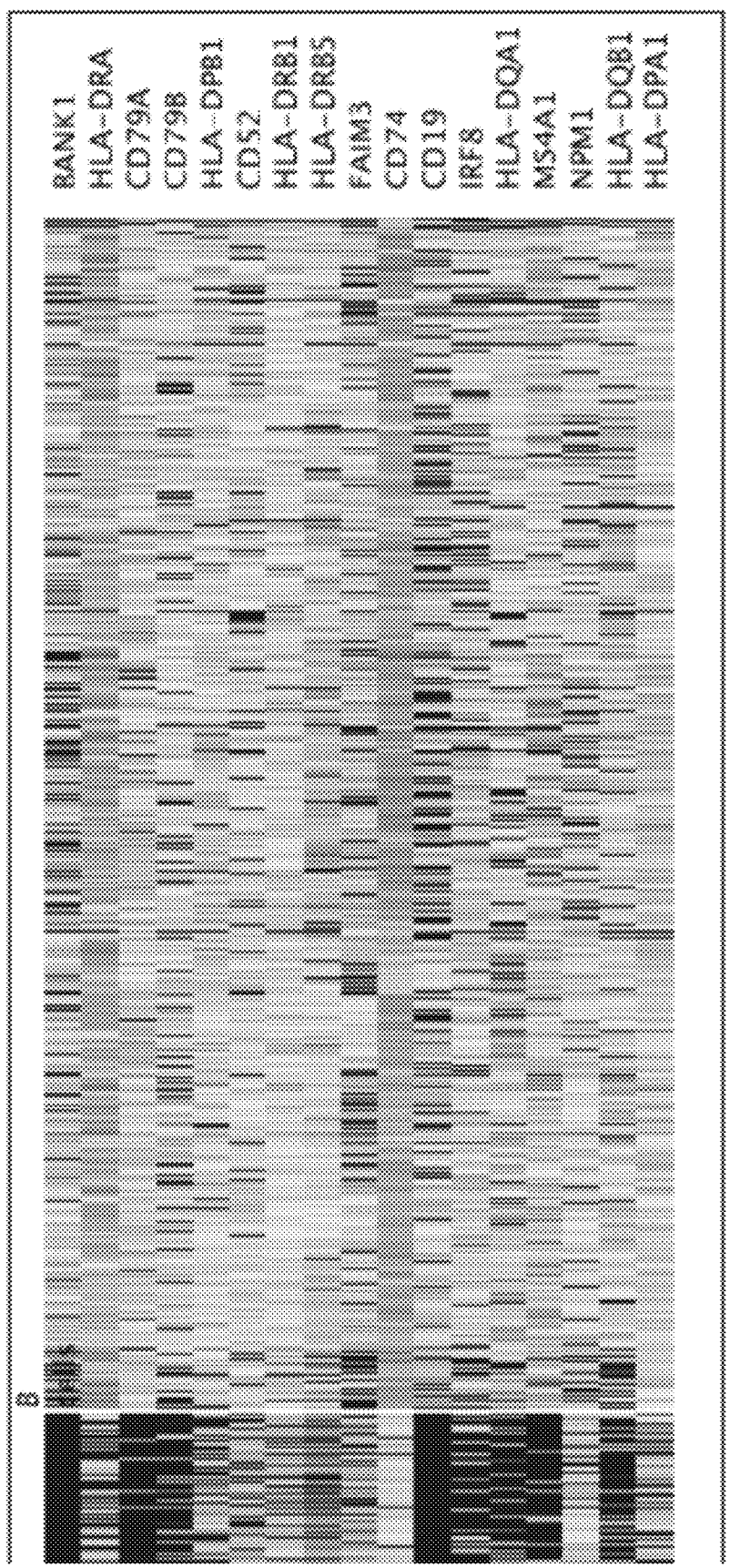

Furthermore, according to another aspect of the disclosed system, reports can be created in a report editor by dragging cell populations from the workspace into the report editor (see FIG. 20A). As another example, cell populations can be overlayed by dragging one cell population on top of another to create 2D overlaps and heatmaps by gene set. Overlays of cell populations are shown in FIG. 20A-D in two ways. In the scatter plot, the different populations are shown as dot plots of different colors in the same graph (and you can choose which population is laid on top of the other). In the heat map, the different populations are organized and appended horizontally as additional columns in the heat map, i.e. all cells of population 1 are rendered together and labeled, followed by all cells of population 2, etc. FIG. 20B shows example heatmaps by gene sets and cell populations. FIG. 20C shows an enlarged view of the leftmost portion of FIG. 20B, and FIG. 20D shows an enlarged view of the rightmost portion of FIG. 20C.

Example Use Case:

As indicated above, the disclosed system provides a powerful mechanism for investigating cellular gene expression data 112 by switching between the cell view mode and gene view mode (or vice versa) while performing gating in those two viewing modes to focus on data of interest.

Figure 21:
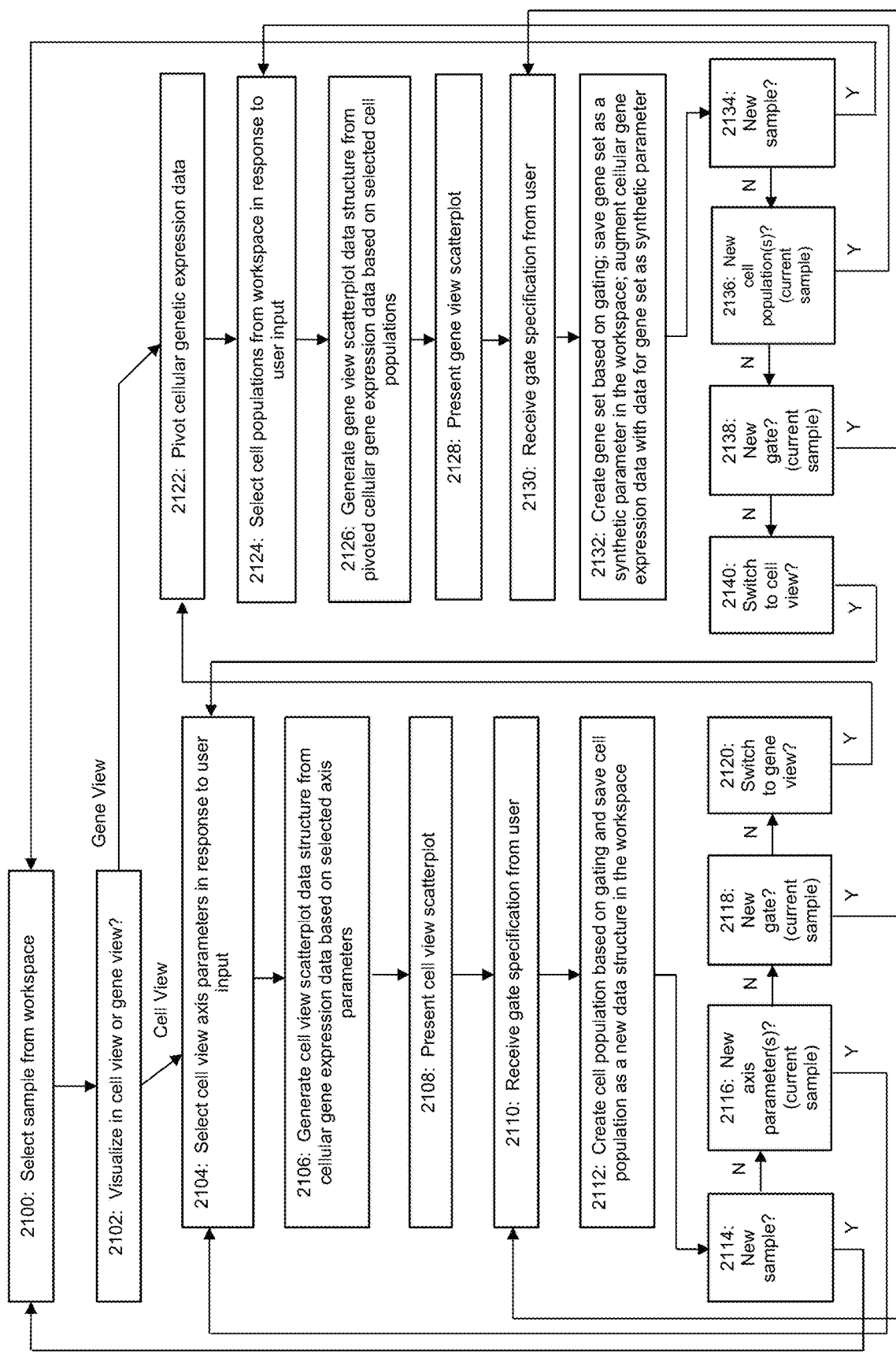
FIG. 21 shows an example process flow for execution by the system to switch between cell view and gene view modes.

FIG. 21 depicts an example process flow for execution as part of program 114 that describes how a user can switch between the cell view mode and gene view mode to support deep investigations of cellular gene expression data. At step 2100, the processor selects a sample from the workspace in response to user input. At step 2102, a decision is made regarding whether to operate in cell view mode or gene view mode. This decision can be made in response to user input.

If a cell view mode is selected, the process flow proceeds to step 2104. If a gene view mode is selected, the process flow proceeds to step 2122. Steps 2104-2120 correspond to operation in the cell view mode, while steps 2122-2140 correspond to operation in the gene view mode.

At step 2104, the processor selects cell view axis parameters in response to user input (e.g., selection of parameters such as genes or gene sets). At step 2106, the processor generates a cell view scatterplot data structure from the cellular gene expression data 112 based on the axis parameters selected at step 2104. This step may involve selecting the columns corresponding to the selected parameters in table 200 to obtain a list of cells and their associated values for each selected parameter. At step 2108, the processor generates the cell view scatterplot 300 from the data within the cell view scatterplot data structure created at step 2106 for presentation to the user.

At step 2110, the processor receives a gate specification with respect to the cell view scatterplot in response to input from a user. This gating creates a cell population (step 2112), where the created cell population gets saved as a new data structure in the workspace. At this point, the user can choose whether to (1) work with a new sample (see step 2114 with progression back to step 2100), (2) define one or more new axis parameters with respect to the current sample while in the cell view mode (see step 2116 with progression back to step 2104), (3) define a new gate with respect to the current sample while in the cell view mode (see step 2118 with progression back to step 2110), or (4) switch to the gene view mode (see step 2120 with progression to step 2122).

At step 2122, the processor pivots the cellular genetic expression data 112 as discussed above. Then, at step 2124, the processor selects cell populations from the workspace in response to user input. At step 2126, the processor generates a gene view scatterplot data structure from the pivoted cellular gene expression data based on the cell populations selected at step 2124. This step may involve selecting the pivoted columns corresponding to the selected cell populations in a pivoted version of table 200 to obtain a list of genes and their associated metrics for each selected cell population. At step 2128, the processor generates the gene view scatterplot 1100 from the data within the gene view scatterplot data structure created at step 2126 for presentation to the user.

At step 2130, the processor receives a gate specification with respect to the gene view scatterplot in response to input from a user. This gating creates a gene set (step 2132), where the created gene set gets saved as a new synthetic parameter in the workspace for association with the cellular genetic expression data. The cellular genetic expression data can thus be augmented with new data values corresponding to the gene set created at step 2132. At this point, the user can choose whether to (1) work with a new sample (see step 2134 with progression back to step 2100), (2) define one or more new cell populations with respect to the current sample while in the gene view mode (see step 2136 with progression back to step 2124), (3) define a new gate with respect to the current sample while in the gene view mode (see step 2138 with progression back to step 2130), or (4) switch to the cell view mode (see step 2140 with progression to step 2104).

Thus, FIG. 21 shows how the system can be used by a user to quickly transition between cell view modes and gene view modes while creating cell populations and gene sets respectively via gating that can be used to aid visualizations after switching between modes.

Figure 22:
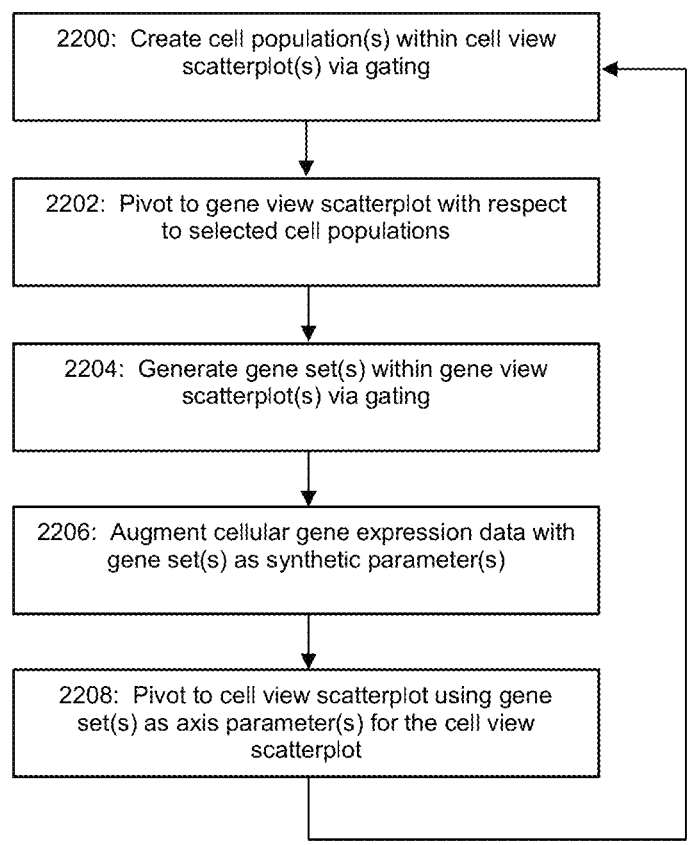
FIG. 22 shows an example of how the system can be operated to switch between cell view and gene view modes to support investigations and research into cell data.

As an example, a powerful and innovative mode of operation is shown by the example process flow of FIG. 22 where a user interacts with program 114 via the process flow of FIGS. 21 to (1) create one or more cell populations within cell view modes of the display (step 2200), (2) pivot to a gene view mode that comparatively displays gene expressions across multiple cell populations (step 2202), (3) create one or more gene sets within gene view mode of the display (step 2204) which augments the cellular gene expression data with the new gene set(s) as a synthetic parameter (step 2206), (4) pivots back to a cell view scatterplot using one or more of these gene sets as axis parameter(s) for a cell view scatterplot (step 2208), and (5) iteratively repeats these operations as desired to drill down into biologically relevant relationships that might exist within the cellular gene expression data 112 (and where operations (1) and (3) may be aided with overlays of user-defined third dimensions on the cell view or gene view data display). For example, the disclosed system can serve as a powerful tool for research into precision/personalized medicine to perform work such as evaluating cell data from numerous patients to find patients with genes that correlate well with survival and therapy response to various cancers or other illnesses/pathologies.

For example, through the tools provided herein, a user might be able to analyze cell populations to identify differentially expressed gene sets that are correlated to better chances for survival with respect to a particular Cancer X (which we can label as "Survival Gene Set"). At the same time, a user might be able to analyze cell populations to identify differentially expressed gene sets that are correlated to poor chances for survival with respect to Cancer X (which we can label as "Not Survival Gene Set"). Further still, a user might be able to analyze cell populations to identify differentially expressed gene sets that are correlated to responding well to Therapy Y for Cancer X (which we can label "Therapy Responsive Gene Set"). Then, these gene sets can be used as synthetic parameters in the cell view mode of the system to find cell populations in patients that are genetically predisposed to respond well to treatment by Therapy Y in order to survive Cancer X. For example, the cell view scatterplot can use the Survival Gene Set as one axis parameter (e.g., X-axis parameter) and the Not Survival Gene Set as the other axis parameter (e.g., Y-axis parameter), while using the Therapy Responsive Gene Set as the third dimensional overlay. The resultant scatterplot can show cell populations that will correlate well with both survival and therapy responsiveness (as well as cell populations that do not correlate well with survival or therapy responsiveness).

While the invention has been described above in relation to its example embodiments, various modifications may be made thereto that still fall within the invention's scope. For example, while the example scatterplots shown herein present the X-axis as a horizontal axis and the Y-axis as a vertical axis, it should be understood that some practitioners may find it desirable to tilt the scatterplots. An example would a scenario where the diagonal y=x is deemed biologically important. In such a case, the scatterplot might be tilted so that the y=x diagonal is presented as a horizontal or vertical line rather than a 45 degree line to thereby help focus users on how far data might lie away from the y=x line. Accordingly, it should be understood that these and other modifications to the invention will be recognizable upon review of the teachings herein.

What is claimed is:

1. A computing-implemented method of visualizing a multi-parameter data set performed by one or more processors executing program instructions, the method comprising:

receiving a multi-parameter data set comprising cellular gene expression data generated by flow cytometry equipment based on a plurality of cells, the multi-parameter data set including a plurality of data items, each data item associated with a plurality of parameters corresponding to expression of a plurality of genes and including data values for each of the associated parameters;

providing a user interface to a user for visualizing the multi-parameter data set across a first axis and a second axis, wherein the user interface is configured to enable the user to select a first parameter from among the plurality of parameters to associate with the first axis and a second parameter from among the plurality of parameters to associate with the second axis;

receiving a first user input from the user via the user interface, wherein the first user input comprises a selection of a first parameter associated with the first axis and a second parameter associated with the second axis;

generating, within the user interface, a cell view scatterplot of the multi-parameter data set across the first and second axes, wherein the first and second axes correspond to the user-selected first and second parameters within the multi-parameter data set, the cell view scatterplot comprising a first plurality of dots, each dot in the first plurality of dots corresponding to a data item from the multi-parameter data set and being positioned on the cell view scatterplot at a position along the first and second axes at a location corresponding to the data values for the parameters corresponding to the axes;

receiving a second user input from the user via the user interface, wherein the second user input comprises a selection of a first cell population associated with the first axis and a second cell population associated with the second axis;

in response to receiving the second user input, pivoting from the cell view scatterplot to a gene view scatterplot by generating, within the user interface, the gene view scatterplot comprising a second plurality of dots, wherein the second plurality of dots correspond to a plurality of different genes expressed by the first and the second cell populations, and each dot of the second plurality of dots is positioned on the first and second axis of the gene view scatterplot based on expression of the corresponding gene by the first and second cell populations;

receiving, from the user via the user interface, a gate creation input defining a gated gene set comprising a subset of the plurality of different genes;

creating a synthetic parameter data object in a workspace, the synthetic parameter data object comprising, for individual cells of the plurality of cells, synthetic parameter values calculated based on two or more genes from the gated gene set;

augmenting the cellular gene expression data such that the synthetic parameter values are associated with cells in the cellular gene expression data; and displaying, within the user interface, a second cell view scatterplot presenting a focused view of a cluster of cells, at least the first axis or the second axis in the second cell view scatterplot corresponding to the synthetic parameter.

2. The method of claim 1, wherein the data values for each of the parameters comprise data indicative of counts for expressions of the corresponding genes in the cell corresponding to that particular data item.

3. The method of claim 2, wherein the gene view scatterplot is generated from the cellular gene expression data based on user specification of a plurality of cell populations.

4. The method of claim 3, wherein the pivoting from the cell view scatterplot to the gene view scatterplot is performed in response to the user specification of the plurality of cell populations.

5. The method of claim 3, further comprising:
generating a gene set by gating a plurality of genes in the gene view scatterplot.

6. The method of claim 5, further comprising:
pivoting to the cell view scatterplot from the gene view scatterplot based on a user specification of a gene set for use as an axis parameter in the cell view scatterplot.

7. The method of claim 2, wherein the cellular gene expression data comprises a plurality of stochastic labels derived from stochastic labeling of a sample.

8. The method of claim 1, further comprising:
receiving, via the user interface, a user specification of a new first parameter associated with the first axis; and
updating, within the user interface, the cell view scatterplot based on the user specification of the new first parameter associated with the first axis of the cell view scatterplot.

9. The method of claim 1, further comprising repeating the creating, translating, and presenting steps to create a plurality of data objects in the workspace that represent a plurality of cell populations.

10. The method of claim 1, further comprising:
gating a group of dots in the second cell view scatterplot based on the defined gene set to define another cell population; and
creating a data object in the workspace that is representative of the defined another cell population.

11. An apparatus comprising:
a memory configured to store a multi-parameter data set;
a processor for cooperation with the memory, the processor configured to perform the method of claim 1, and
a display in cooperation with the processor, wherein the display is configured to graphically present the cell view scatterplot and the gene view scatterplot.

12. The apparatus of claim 11, wherein the multi-parameter data set comprises cellular gene expression data, the data items comprising a plurality of cells, wherein the parameters comprise a plurality of genes, and wherein the data values for each of the parameters associated with a particular data item comprise data indicative of counts for expressions of the corresponding genes in the cell corresponding to that particular data item.

13. The method of claim 1, wherein the cell view scatterplot or the second cell view scatterplot comprises at least a first subset of dots corresponding to cells having a zero value for at least the parameter corresponding to the first axis and a second subset of dots corresponding to cells having a zero value for at least the parameter corresponding to the second axis.

14. The method of claim 13, further comprising displaying the cell view scatterplot or the second cell view scatterplot in a spread zeros format comprising:
a first two-dimensional quadrant containing dots having a zero value for the parameters corresponding to both the first axis and the second axis;
a second two-dimensional quadrant containing dots having a zero value for the parameter corresponding to the first axis and positive values for the parameter corresponding to the second axis;

a third two-dimensional quadrant containing dots having positive values for the parameter corresponding to the first axis and a zero value for the parameter corresponding to the second axis; and a fourth two-dimensional quadrant containing dots having positive values for the parameters corresponding to both the first axis and the second axis.

15. The method of claim 1, wherein the synthetic parameter values are calculated based on a summation of the two or more genes from the gated gene set.

16. A computer program product comprising:

a plurality of processor-executable instructions that are resident on a non-transitory computer readable storage medium, wherein the instructions are configured, upon execution by a processor, to cause the processor to:

receive a multi-parameter data set comprising cellular gene expression data generated by flow cytometry equipment based on a plurality of cells, the multi-parameter data set including a plurality of data items, each data item associated with a plurality of parameters corresponding to expression of a plurality of genes and including data values for each of the associated parameters;

provide a user interface to a user for visualizing the multi-parameter data set across a first axis and a second axis, wherein the user interface is configured to enable the user to select a first parameter from among the plurality of parameters to associate with the first axis and a second parameter from among the plurality of parameters to associate with the second axis;

receive a first user input from the user via the user interface, wherein the first user input comprises a selection of a first parameter associated with the first axis and a second parameter associated with the second axis;

generate, within the user interface, a cell view scatterplot of a multi-parameter data set across the first and second axes, wherein the first and second axes correspond to user-selected first and second parameters within the multi-parameter data set, the cell view scatterplot comprising a first plurality of dots, each dot in the first plurality of dots corresponding to a data item from the multi-parameter data set and being positioned on the cell view scatterplot at a position along the first and second axes at a location corresponding to the data values for the parameters corresponding to the axes;

receive a second user input from the user via the interface, wherein the second user input comprises a selection of a first cell population associated with the first axis and a second cell population associated with the second axis;

in response to receiving the second user input, pivot from the cell view scatterplot to a gene view scatterplot by generating, within the user interface, the gene view scatterplot comprising a second plurality of dots, wherein the second plurality of dots correspond to a plurality of different genes expressed by the first and the second cell populations, and each dot of the second plurality of dots is positioned on the first and second axis of the gene view scatterplot based on expression of the corresponding gene by the first and second cell populations;

receiving, from the user via the user interface, a gate creation input defining a gated gene set comprising a subset of the plurality of different genes;

create a synthetic parameter data object in a workspace, the synthetic parameter data object comprising, for individual cells of the plurality of cells, synthetic parameter values calculated based on two or more genes from the gated gene set;

augment the cellular gene expression data such that the synthetic parameter values are associated with cells in the cellular gene expression data; and display, within the user interface, a second cell view scatterplot presenting a focused view of a cluster of cells, at least the first axis or the second axis in the second cell view scatterplot corresponding to the synthetic parameter.

17. The computer program product of claim 16, wherein the instructions are further configured to cause the processor to:

generate a gene view scatterplot of cellular gene expression data based on user specification of a plurality of cell populations.

18. The computer program product of claim 16, wherein the instructions are further configured to cause the processor to:

pivot to a cell view scatterplot from the gene view scatterplot based on a user specification of a gene set for use as an axis parameter in the cell view scatterplot.

19. The computer program product of claim 16, wherein the cell view scatterplot or the second cell view scatterplot comprises at least a first subset of dots corresponding to cells having a zero value for at least the parameter corresponding to the first axis and a second subset of dots corresponding to cells having a zero value for at least the parameter corresponding to the second axis.

20. The computer program product of claim 19, wherein the instructions are further configured to cause the processor to display the cell view scatterplot or the second cell view scatterplot in a spread zeros format comprising:

a first two-dimensional quadrant containing dots having a zero value for the parameters corresponding to both the first axis and the second axis;

a second two-dimensional quadrant containing dots having a zero value for the parameter corresponding to the first axis and positive values for the parameter corresponding to the second axis;

a third two-dimensional quadrant containing dots having positive values for the parameter corresponding to the first axis and a zero value for the parameter corresponding to the second axis; and a fourth two-dimensional quadrant containing dots having positive values for the parameters corresponding to both the first axis and the second axis.

21. The computer program product of claim 16, wherein the synthetic parameter values are calculated based on a summation of the two or more genes from the gated gene set.

22. A system comprising:

one or more processors; and a non-transitory computer readable storage medium having stored thereon computer-executable instructions that, upon execution by the one or more processors, cause the one or more processors to:

receive a multi-parameter data set comprising cellular gene expression data generated by flow cytometry equipment based on a plurality of cells, the multi-parameter data set including a plurality of data items, each data item associated with a plurality of parameters corresponding to expression of a plurality of genes;

provide a user interface to a user for visualizing the multi-parameter data set across a first axis and a second axis, wherein the user interface is configured to enable the user to select a first parameter from among the plurality of parameters to associate with a first axis and a second parameter from among the plurality of parameters to associate with a second axis;

receive a first user input from the user via the user interface, wherein the first user input comprises a selection of a first parameter associated with the first axis and a second parameter associated with the second axis;

generate, within the user interface, a cell view scatterplot of a multi-parameter data set across the first and second axes, wherein the first and second axes correspond to user-selected first and second parameters within the multi-parameter data set, the cell view scatterplot comprising a first plurality of dots, each dot in the first plurality of dots corresponding to a data item from the multi-parameter data set and being positioned on the cell view scatterplot at a position along the first and second axes at a location corresponding to the data values for the parameters corresponding to the axes;

receive a second user input from the user via the interface, wherein the second user input comprises a selection of a first cell population associated with the first axis and a second cell population associated with the second axis;

in response to receiving the second user input, pivot from the cell view scatterplot to a gene view scatterplot by generating, within the user interface, the gene view scatterplot comprising a second plurality of dots, wherein the second plurality of dots correspond to a plurality of different genes expressed by the first and the second cell populations, and each dot of the second plurality of dots is positioned on the first and second axis of the gene view scatterplot based on expression of the corresponding gene by the first and second cell populations;

receive, from the user via the user interface, a gate creation input defining a gated gene set comprising a subset of the plurality of different genes;

create a synthetic parameter data object in a workspace, the synthetic parameter data object comprising, for individual cells of the plurality of cells, synthetic parameter values calculated based on two or more genes from the gated gene set;

augment the cellular gene expression data such that the synthetic parameter values are associated with cells in the cellular gene expression data; and display, within the user interface, a second cell view scatterplot presenting a focused view of a cluster of cells, at least the first axis or the second axis in the second cell view scatterplot corresponding to the synthetic parameter.

23. The system of claim 22, wherein the cell view scatterplot or the second cell view scatterplot comprises at least a first subset of dots corresponding to cells having a zero value for at least the parameter corresponding to the first axis and a second subset of dots corresponding to cells having a zero value for at least the parameter corresponding to the second axis.

24. The system of claim 23, wherein the instructions are further configured to cause the one or more processors to display the cell view scatterplot or the second cell view scatterplot in a spread zeros format comprising:

a first two-dimensional quadrant containing dots having a zero value for the parameters corresponding to both the first axis and the second axis;

a second two-dimensional quadrant containing dots having a zero value for the parameter corresponding to the first axis and positive values for the parameter corresponding to the second axis;

a third two-dimensional quadrant containing dots having positive values for the parameter corresponding to the first axis and a zero value for the parameter corresponding to the second axis; and a fourth two-dimensional quadrant containing dots having positive values for the parameters corresponding to both the first axis and the second axis.

25. The system of claim 22, wherein the synthetic parameter values are calculated based on a summation of the two or more genes from the gated gene set.

* * * * *